(12) United States Patent
Wang et al.

(10) Patent No.: US 8,148,528 B2
(45) Date of Patent: Apr. 3, 2012

(54) PROCESSES AND COMPOUNDS FOR THE PREPARATION OF NORMORPHINANS

(75) Inventors: Peter X. Wang, Clarkson Valley, MO (US); Frank W. Moser, Arnold, MO (US); Gary L. Cantrell, Troy, MO (US); Tao Jiang, St. Louis, MO (US); Robert E. Halvachs, Belleville, IL (US); Christopher W. Grote, Webster Groves, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 334 days.

(21) Appl. No.: 12/469,951

(22) Filed: May 21, 2009

(65) Prior Publication Data

US 2009/0299069 A1 Dec. 3, 2009

Related U.S. Application Data

(60) Provisional application No. 61/056,079, filed on May 27, 2008.

(51) Int. Cl.
*C07D 489/08* (2006.01)
(52) U.S. Cl. .................................................. 546/46
(58) Field of Classification Search .................. None
See application file for complete search history.

(56) References Cited

U.S. PATENT DOCUMENTS

| | | | |
|---|---|---|---|
| 3,101,339 A | 8/1963 | Zeile et al. |
| 4,141,897 A | 2/1979 | Olofson et al. |
| 4,176,186 A | 11/1979 | Goldberg et al. |
| 4,322,426 A | 3/1982 | Hermann et al. |
| 4,368,326 A | 1/1983 | Rice |
| 4,410,700 A | 10/1983 | Rice |
| 4,521,601 A | 6/1985 | Rice |
| 4,535,157 A | 8/1985 | Meltzer et al. |
| 4,556,712 A | 12/1985 | Rice |
| 4,613,668 A | 9/1986 | Rice |
| 4,727,146 A | 2/1988 | Rice |
| 4,794,186 A | 12/1988 | Oine et al. |
| 5,112,975 A | 5/1992 | Wallace |
| 5,240,933 A | 8/1993 | Merz et al. |
| 5,352,680 A | 10/1994 | Portoghese et al. |
| 5,574,159 A | 11/1996 | Chang et al. |
| 5,668,285 A | 9/1997 | Rice et al. |
| 5,869,669 A | 2/1999 | Huang et al. |
| 5,907,069 A | 5/1999 | Becnel et al. |
| 5,922,876 A | 7/1999 | Huang et al. |
| 5,948,788 A | 9/1999 | Huang et al. |
| 5,952,495 A | 9/1999 | Huang et al. |
| 5,981,474 A | 11/1999 | Manning et al. |
| 6,008,354 A | 12/1999 | Huang et al. |
| 6,008,355 A | 12/1999 | Huang et al. |
| 6,013,796 A | 1/2000 | Huang et al. |
| 6,136,817 A | 10/2000 | Schmidhammer |
| 6,174,891 B1 | 1/2001 | Nagase et al. |
| 6,365,742 B1 | 4/2002 | Mudryk et al. |
| 2005/0182258 A1 | 8/2005 | Schmidhammer et al. |
| 2007/0265293 A1 | 11/2007 | Boyd et al. |
| 2008/0064712 A1 | 3/2008 | Schmidhammer et al. |
| 2008/0146804 A1 | 6/2008 | Stumpf |
| 2008/0207906 A1 | 8/2008 | Wang et al. |
| 2009/0270624 A1 | 10/2009 | Weigl et al. |

FOREIGN PATENT DOCUMENTS

| | | |
|---|---|---|
| EP | 0 028 959 | 1/1985 |
| ES | 2 121 554 | 11/1998 |
| PL | 124 001 | 7/1985 |
| WO | WO 01/55117 | 8/2001 |
| WO | WO 2004/029059 | 4/2004 |
| WO | WO 2004/043964 | 5/2004 |
| WO | WO 2005/077957 A2 | 8/2005 |
| WO | WO 2006/084389 | 8/2006 |
| WO | WO 2006/127899 | 11/2006 |
| WO | WO 2006/138020 | 12/2006 |
| WO | WO 2006138020 A2 * | 12/2006 |

OTHER PUBLICATIONS

Amaravathi et al., "Oxidation of 1-benzyl-3,4-dihydroisoquinolines using active manganese dioxide," Indian Journal of Chemistry, Section B: Organic Chemistry Including Medicinal Chemistry (1983), 22B(12), 1246-7.

Andreu et al., "An efficient method for the preparation of antitumoral α-keto-imines benzyldihydroisoquinolines by selective benzylic oxidation with C/Pd in acetonitrile," Tetrahedron Letters (2002), 43(5), 757-759.

Archer et al., "1-Acetamido-17-carbomethoxydihydrothebainone," Journal of Heterocyclic Chemistry (1981), 18(2), 357-61.

Baxendale et al., "Enantioselective synthesis of the tetrahydrobenzylisoquinoline alkaloid (−)-norarmepavine using polymer supported reagents," Heterocycles (2003), 60(12), 2707-2715.

Benosman et al., "Synthesis of isoquinolines isolated fro *Aniba canelilla*", Comptes Rendus de l'Academie des Sciences, Serie II:Mecanique, Physique, Chimie, Sciences de la Terre et de l'Univers, 19983, 316(4), pp. 465-468 (French Language).

Bentley et al., The Reduction of Thebaine and Dihydrothebaine by Sodium and Ammonia, Journal of the Chemical Society, Abstracts (1952), pp. 958-966.

Bermejo et al., "Syntheses and antitumor targeting G1 phase of the cell cycle . . . ", Journal of Medicinal Chemistry, 2002, 45(23), pp. 5058-5068.

Beyerman et al., Recl. Trav. Chim. Pays-Bas., 1976, 95, pp. 184.

Bhakuni et al., "Sunthesis of (±)-12-amino derivatives of scoulerine, . . . ", Indian Journal of Chemistry, Section B: Organic chemistry Including Medicinal Chemistry, 1985, 246(6), pp. 596-601.

Bhakuni et al., "Studies on mannich reaction of 1-benzyltetrahydroisoquinolines", Journal of the Indian Chemical Society, 1988, 65(6), pp. 417-421.

Bjorklund et al., "Cryptic Stereochemistry of Berberine alkaloid biosynthesis", Journal of the American Chemical Society, 1995, 117(5), pp. 1533-1545.

Boehme et al., "Analogs of M4 selective synthetic muscarinic receptor antagonists: . . . ", Medicinal Chemistry Research, 2002, 11(8), pp. 423-433.

(Continued)

*Primary Examiner* — Kamal Saeed
*Assistant Examiner* — Nyeemah A Grazier

(57) ABSTRACT

The invention generally provides processes and intermediate compounds useful for the production of normorphinans and derivatives of normorphinans.

17 Claims, No Drawings

OTHER PUBLICATIONS

Bognar et al., "Selective Quaternization in the Morphine Series", Tetrahedron Letters, 1964, No. 39, pp. 2867-2871.

Cave et al., "Alkaloids of cryptocarya phyllostemon", Australian Journal of Chemistry, 1989, 42(12), pp. 2243-2263.

Chackalamannil et al., "The synthesis of erythro- and threo-N-methyl-7-hydroxy-1,2,9,10-tetramethoxyaporphine", Tetrahedron Letters, 1980, 21(21), pp. 2029-2032.

Chazerain, "1-Benzoylisoquinolines and their transformation into 1-phenyl-3-benzazepines", Ann. Chim. (Paris), 1963, 8, pp. 255-284.

Cho et al., "Synthesis of 6,7-dimethoxy-1-halobenzyl-1,2,3,4-tetrahydroisoquinolines," Journal of Heterocyclic Chemistry (1999), 36(5), 1151-1156.

Chrzanowska et al., "Asymmetric synthesis of isoquinoline alkaloids," Chemical Reviews (2004), 104, 3341-3370.

Chrzanowska et al., "Synthesis of (S)-(−)- and (R)-(+)-O-methylbharatamine using a diastereoselective Pomeranz-Fritsch-Bobbitt methodology," Tetrahedron: Asymmetry (2005), 16(17), 2954-2958.

Coutts et al., "The enzymatic oxidation of phenolic tetrahydroisoquinoline-1-carboxylic acids," Journal of the Chemical Society, Perkin Transactions 1: Organic and Bio-Organic Chemistry (1972-1999) (1979), (11), 2744-50.

Crooks et al., "Opiate receptor binding properties of morphine-, dihydromorphine-, and codeine 6-O-sulfate ester congeners", Bioorganic & Medicinal Chemistry Letters, 16, 2006, pp. 4291-4295.

Czarnocki, "Enantioselective syntheis of (R)-(−)-calycotomine and (S)-(−)-xylopinine from D-ribonolactone", Journal of Chemical Research, Synopses, 1992, 10, pp. 334-335.

Czarnocki et al., "Asymmetric synthesis of isoquinoline alkaloids. (R)- and (S)-2-(ethoxycarbonyl)-1-formyl-6, . . . ", bulletin des Societes Chimiques Beiges, 1986, 95(9-10), pp. 749-770.

Davis et al., "Synthesis of the orotoberberine alkaloid (S)-(−)-xylopinine using enantiopure sulfinimines", Journal of Organic Chemistry, 2002, 67(4), pp. 1290-1296.

DeGraw et al., J. Het. Chem., Jun. 1974, pp. 363.

Fry et al., Mannich Derivatives of Analgesic Agents, Journal of Organic Chemistry (1959), 24, pp. 116-117.

Funke et al., A$^1$H and $^{13}$C Nuclear Magnetic Resonance Study of Three Quaternary Salts of Naloxone and Oxymorphone, J. Chem. Soc. Perkin Trans. (1986) 2, pp. 735-738.

Giger et al., Synthesis and Reactions of the diels-Alder Adduct of Thebaine with 4-phenyl-1,2,4-triazoline-3,5-dione, Tetrahedron (1973), 29(16), pp. 2387-2391.

Gupta et al., "Synthetic photochemistry: Synthesis of liriodenine," Indian Journal of Chemistry, Section B: Organic Chemistry Including Medicinal Chemistry (1983), 22B(5), 429-31.

Hanaoka et al., "Chemical transformation of protoberberines. VIII. A novel synthesis of (±)-fumaricine and a formal synthesis of (±)-alpinigenine," Chemical and Pharmaceutical Bulletin (1985), 33(6), 2273-80.

Hirai et al., "A new preparation of an ochotensin-type isoquinoline by photolysis," Heterocycles (1984), 22(6), 1359-62.

Hu et al., "Photosynthesis of tetrahydroprotoberberines with electron-withdrawing groups on ring D," Chinese Chemical Letters (1998), 9(8), 707-710.

Iorio et al., "Diastereoisomeric Quaternary Morphinium Salts: Synthesis, Stereochemistry and Analgesic Properties", European Journal of Medicinal Chemistry, 1984, 19(1), pp. 11-16.

Kaldor et al., "Stereocontrolled synthesis of cis-dibenzoquinolizine chlorofumarates: curare-like agents of ultrashort duration," Journal of Organic Chemistry (2001), 66(10), 3495-3501.

Kametani et al., "Studies on the syntheses of heterocyclic compounds. DCXCII. A novel synthetic route to phthalideisoquinoline and spirobenzylisoquinoline type alkaloids," Chemical and Pharmaceutical Bulletin (1977), 25(2), 321-6.

Kametani et al., "Studies on the syntheses of heterocyclic compounds. DCXCII. A stereoselective Total Synthesis of (±)-Ophiocarpine; a Simple Route to 13-Hydroxyberbines", JCS Perkin I, 1977, pp. 376-382.

Kametani et al., "Studies on the syntheses of heterocyclic compounds. DCXCIII. A total synthesis of atheroline by photolysis," Tetrahedron (1977), 33(9), 1069-71.

Kametani et al., "Synthesis of oxoaporphine by photolysis. Total synthesis of atheroline," Heterocycles (1975), 3(10), 821-5.

Kapadia et al., "Facile oxidative formation of O-methylvelucryptine during synthesis of dl-O-methylarmepavine," Indian Journal of Pharmaceutical Sciences (1992), 54(6), 227-33.

Kessar et al., "Synthetic Photochemistry: Synthesis of (±)-oliveridine," Indian Journal of Chemistry, Section B: Organic Chemistry Including Medicinal Chemistry (1983), 22B(4), 321-4.

Koczka et al., Selective Quaternization of Compounds with Morphine Skeleton, Acta. Chim. Acad. Sci. Hung. (1967), 51(4), pp. 393-402.

Kunitomo et al., "Synthesis of a few trimethoxyoxoaporphines," Yakugaku Zasshi (1979), 99(1), 102-5. (Japanese language).

Kuo et al., "Antiplatelet activity of benzylisoquinoline derivatives oxidized by cerium (IV) ammonium nitrate," Bioorganic and Medicinal Chemistry Letters (2003), 13(16), 2789-2793.

Lebceuf et al., "Velucryptine, A new isoquinoline alkaloid from *Cryptocarya velutinosa*," Journal of Natural Products (1989), 52(3), 516-21.

Lenz et al., "Lead tetraacetate mediated oxidation of the enamides derived from 1-benzyl-3,4-dihydroisoquinolines," Journal of Organic Chemistry (1988), 53(6), 1176-83.

Lenz et al., "Synthesis of the novel isoquinoline enamide alkaloid polycarpine," Journal of Heterocyclic Chemistry (1981), 18(4), 691-3.

Lopez et al., Photoxidation of Thebaine. A Route to 14-Hydroxymorphinones and Hydrodibenzofuran Analogs of Methadone, Tetrahedron Letters (1994), 35(31), pp. 5727-5730.

Lopez et al., The [4+2] Addition of Singlet Oxygen to Thebaine: New Access to Highly Functionalized Morphine Derivatives via Opioid Endoperoxides, J. Org. Chem. (2000), 65(15), pp. 4671-4678.

Manoharan et al., "Convenient Method for Replacement of Tertiary N-Methyl by Other Alkyl Groups: Application to Morphine Alkaloids", Indian Journal of Chemistry, 1984, vol. 19, No. 1, pp. 5-11.

Manoharan et al., Stereoselectivity in Quaternization of Thebaine: 270 MHz PMR Spectroscopic Studies, Indian Journal of Chemistry, Section B: Organic Chemistry Including Medicinal chemistry (1987), 26B(2), pp. 140-142.

Markaryan et al., "Isoquinoline derivatives. XI. Synthesis and pharmacological activity of 1-arylalkyl-4-spirocydohexane-6,7-dimethoxy-1,2,3,4-tetrahydroisoquinolines and some of their derivatives," Armyanskii Khimicheskii Zhurnal (1975), 28(10), 829-35. (Russian language).

Martin et al., "Oxidation of imines by selenium dioxide," Zeitschrift fuer Naturforschung, Teil B: Anorganische Chemie, Organische Chemie (1986), 41B(10), 1260-4.

Martin et al., "Regiospecific oxidation of substituted 1-benzyl-3,4-dihydroisoquinolines using singlet oxygen," Tetrahedron Letters (1980), 21(27), 2613-16.

Martin et al., "Synthesis and photooxygenation of some substituted 1-benzyl-3,4-dihydroisoquinolines. Mechanism of enamine photooxygenation," Helvetica Chimica Acta (1982), 65(3), 762-74.

McMahon et al., "Rearrangement of 1-(α-hydroxybenzyl)-1,2,3,4-tetrahydroisoquinolines to 1-phenyl-2,3,4,5-tetrahydro-1H-3-benzazepines," Journal of the Chemical Society, Perkin Transactions 1: Organic and Bio-Organic Chemistry (1972-1999) (1982), (9), 2163-7.

Memetzidis et al., "Synthesis of aromatic chloroberbines," Heterocycles (1990), 31(2), 341-51.

Meuzelaar et al., "Chemistry of opium alkaloids. Part 45. Improvements in the total synthesis of morphine," European Journal of Organic Chemistry (1999), 2315-2321.

Meyers et al., "Asymmetric synthesis of isoquinoline alkaloids", Tetrahedron, 1987, 43(21), pp. 5095-5108.

Meyers et al., "High enantioselective alkyation of tetrahydroisoquinolines with a chiral valinol derivative . . . ", Angewandte Chemie, 1984, 16(6), pp. 448-449.

Miller et al., "Synthesis and biological evaluation of fragmented derivatives of tetrahydroisoquinolines. 2. Trimetoquinol studies", Journal of Medicinal Chemistry, 1975, 18(5), pp. 454-457.

Mujahidin et al., "Enantioselective synthesis of (+)-(S)-laudanosine and (−)-(S)-xylopinine," European Journal of Organic Chemistry (2005), 2689-2693.

Musich et al., Reaction of O-methyl-N, $N^1$-Diisopropylisourea with Amino Acids and Amines, Journal of Organic Chemistry (1977), 42(1), pp. 139-141.

Nagata et al., Synthetic Studies on Isoquinoline Alkaloids. I.* An Efficient Synthesis of 9,10-Substituted Protoberberine Alkaloids 1, Chem. Pharm. Bull., 23(11), 1975, pp. 2867-2877.

Naito et al., "Asymmetric synthesis of dibenzo[a,g]quinolizines related to protoberberine alkaloids," Heterocycles (1983), 20(5), 779-82.

Naito et al., "Reductive photocyclization of enamides and its application to alkaloid synthesis", Kobe Women's Coll. Pharm., Tennen Yuki Kagobutsu Toronkai Koen Yoshishu, $24^{th}$, 1981, pp. 460-465.

Naito et al., "Reductive photocyclization of enamide in the presence of a chrial metal hydride complex . . . ", Kobe Women's Coll. Pharm., Heterocycles, 1981, 16(7), pp. 1141-1143.

Orito et al., "Aryl radical cyclizations of 1-(2'-Bromobenzyl)isoquinolines with AlBN-Bu3SnH: Formation of aporphines and Indolo[2,1-a]isoquinolines," Organic Letters (2000), 2(3), 307-310.

Orito et al., "New synthesis of phthalideisoquinoline alkaloids via a stereoselective hydride reduction of 1-(2'-bromobenzoyl)-3,4-dihydroisoquinoline methiodide, followed by palladium-catalyzed carbonylation aided by chlorotrimethylsilane," Synlett (1994), (4), 245-6.

Orito et al., "Synthesis of (±)-norcoralydine and (±)-tetrahydropalmatine," Organic Preparations and Procedures International (1989), 21(3), 309-14.

Orito et al., "Synthesis of phthalideisoquinoline and protoberberine alkaloids and indolo [2,1-a]isoquinolines in a divergent route involving palladium(0)-catalyzed carbonylation," Journal of Organic Chemistry (1999), 64(18), 6583-6596.

Otto et al., Selection and Amplification of Hosts from Dynamic combinatorial Libraries of Macrocyclic Disulfides, Science (Washington, DC, United States) (2002), 297(5581), pp. 590-593 & Supporting Online Material.

Rice, "Synthetic Opium Alkaloids and Derivatives. A Short total Synthesis . . . ", J. Org. Chem., 1980, 45, pp. 3135-3137.

Rozwadowska et al., "Mammalian alkaloids: O-methylation of (S)- and (R)-dideoxynorlaudanosoline-1-carboxylic acid by catechol O-methyltransferase and identification of a yellow pigment obtained at physiological pH," Helvetica Chimica Acta (1988), 71(7), 1598-607.

Schultz et al., Thebaine Cyclopropanation, Russian Journal of Organic chemistry (Translation of Zhurnal Organicheskoi Khimii) (2003), 39(8), pp. 1083-1088.

Seki, Isao, Studies on the Morphine Alkaloids and its Related Compounds. XIV. Preparation of 6-Amino-hydrophenanthrene Compounds from Hofmann Degradation Products of the Morphine Alkaloids, Chemical & Pharmaceutical Bulletin (1966), 14(5), pp. 453-461.

Shklyaev et al., "A new approach to synthesis of 3,3-dialkyl-3,4-dihydroisoquinoline derivatives," Heteroatom Chemistry (2004), 15(7), 486-493.

Shults et al., Tranformations of Quaternary Tetrahydrothebaine Sulfones, Zh. Org. Khim. (1993), 29(6), pp. 1149-1162, (English pp. 953-963).

Simanek et al., "Synthesis of hypecorine and hypecorinine analogs from 3,4-dihydropapaverine," Symp. Pap. IUPAC Int. Symp. Chem. Nat. Prod., 11th (1978), vol. 2, 58-60.

Simanek et al., "Isolation and chemistry of alkaloids from some plants of the family Papaveraceae. Part LXXIV. Synthesis of hypecorine and hypecorinine analogs from 3,4-dihydropapaverine", Heterocycles, 1978, 9(9), pp. 1233-1240.

Sladkov et al., "2,3,10,11-Tetramethoxy-5,6,7,8,13,13a-hexahydroprotoberberines and their B-seco analogs: Synthesis and antineoplastic activity," Khimiko-Farmatsevticheskii Zhurnal (1989), 23(1), 50-3. (Russian language).

Sladkov et al., "Benzophenanthridines. VI. Conversions of protoberberine alkaloids into benzo[c]phenanthridines. Hofmann degradation of α-N- and β-N-methyl-(±)-13α-hydroxyxylopinine iodides," Zhurnal Organicheskoi Khimii (1989), 25(4), 854-62 (Russian language).

Tolkachev et al., "Application of the Willgerodt-Kindler reaction in the synthesis of the 1-benzyl-1,2,3,4-tetrahydroisoquinoline alkaloids and their derivatives," Symp. Pap. IUPAC Int. Symp. Chem. Nat. Prod., 11th (1978), vol. 3, 47-50.

Trifonov et al., "Application of organic photochemistry in the synthesis of (±)-glaucine," Izvestiya po Khimiya (1978), 11(2), 297-304.

Trifonov et al., "Berbin-8-ones from 2'-halo-1-benzylisoquinolines and metal carbonyls," Tetrahedron Letters (1985), 26(26), 3159-62.

Uematsu et al., "Asymmetric transfer hydrogenation of imines," Journal of the American Chemical Society (1996), 118, 4916-4917.

Walterova et al., "Isolation and chemistry of the alkaloids from some plants of the genus Papaver. LXXVII. Pseudobase formation in 2-methylpapaverinium cations and their biotransformation by enzymes of rat liver homogenates in vitro," Collection of Czechoslovak Chemical Communications (1980), 45(3), 956-65.

Wert et al., "Hofmann degradation of β-hydroxy ammonium salts. α- and β-hydroxylaudanosine, 7-hydroxyglaucine, and 13-hydroxyxylopinine," Journal of Organic Chemistry (1982), 47(26), 5141-50.

Williams et al., "One-pot formation of nitrogen-containing heterocyclic ring systems using a deprotection-cyclization-asymmetric reduction sequence," Chemical Communications Cambridge, United Kingdom) (2005), (37), 4735-4737.

Yamada et al., "Studies on 1,2,3,4-tetrahydroisoquinolines. VI. Reutilization of the unwanted (R)-isomer of (S)-(−)-5,7-dihydroxy-1-(3,4,5-trimethoxybenzyl)-1,2,3,4-tetrahydroisoquinoline (TA-073)," Chemical and Pharmaceutical Bulletin (1983), 31(1), 70-4.

Zhao et al., "Synthesis of nitrones from 3,4-dihydroisoquinoline derivatives by oxidation with m-chloroperoxybenzoic acid," Organic Preparations and Procedures International (1997), 29(2), 185-194.

Ninan et al., "An Improved Synthesis of Noroxymorphone", Tetrahedron, vol. 48, No. 32, Jan. 1, 1992, pp. 6709-6716, XP002144371.

* cited by examiner

PROCESSES AND COMPOUNDS FOR THE PREPARATION OF NORMORPHINANS

CROSS-REFERENCE TO RELATED APPLICATIONS

This application claims priority from Provisional Application Ser. No. 61/056,079 filed on May 27, 2008, which is hereby incorporated by reference in its entirety.

FIELD OF THE INVENTION

The present invention generally relates to processes and intermediate compounds useful for the production of normorphinans and derivatives of normorphinans.

BACKGROUND OF THE INVENTION

Noroxymophone is a common starting material to make a series of semi-synthetic opiate N-substituted derivatives (i.e., "nal" compounds) such as naltrexone and naloxone. Noroxymorphone is currently produced in a multi-step process from a poppy derived opiate. As demand of these semi-synthetic opiate derivatives has increased, there is a need for noroxymorphone to be produced more efficiently and at higher purity.

SUMMARY OF THE INVENTION

The present invention provides processes and compounds for the preparation of normorphinan compounds. Among the various aspects of the invention is a provision for compound comprising Formula 21a:

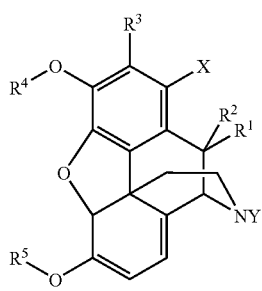

21a wherein:
- $R^1$ and $R^2$ are independently chosen from hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group chosen from =O, =S, cycloalkyl ketal, cycloalkyl thiol ketal, and cycloalkyl dithiol ketal;
- $R^3$ is chosen from hydrogen, halogen, OH, $NH_2$, CN, $CF_3$, $SO_2R^8$, hydrocarbyl, and substituted hydrocarbyl;
- $R^4$ and $R^5$ are independently chosen from —$(CH_2)_n CH_3$ and $CH_3$;
- $R^8$ is chosen from hydrocarbyl and substituted hydrocarbyl;
- X is halogen; and
- Y is chosen from an aryl group, a benzyl group, an acyl group, a formyl ester, an alkoxycarbonyl group, a benzyloxycarbonyl group, an alkylamidocarbonyl group, a trialkylsilyl group, an alkylsulfonyl group, and an aryl sulfonyl group; and
- n is an integer from 1 to 8.

Another aspect of the invention encompasses compound comprising Formula 25:

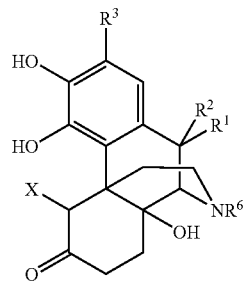

25 wherein:
- $R^1$ and $R^2$ are independently chosen from hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair) and wherein $R^1$ and $R^2$ together may form a group chosen from =O, =S, cycloalkyl ketal, cycloalkyl thiol ketal, and cycloalkyl dithiol ketal;
- $R^3$ is chosen from hydrogen, halogen, OH, $NH_2$, CN, $CF_3$, $SO_2R^8$, hydrocarbyl, and substituted hydrocarbyl;
- $R^6$ is chosen from hydrogen, an alkyl group, an allyl group, a cycloalkylmethyl group, an aryl group, a benzyl group, and $C(O)_n R^7$;
- $R^7$ is chosen from an alkyl group, an aryl group, and a benzyl group;
- $R^8$ is chosen from hydrocarbyl and substituted hydrocarbyl;
- X is halogen; and
- n is an integer from 1 to 2.

Still another aspect provides a process for the preparation of compound 21, the process comprising the following reaction scheme:

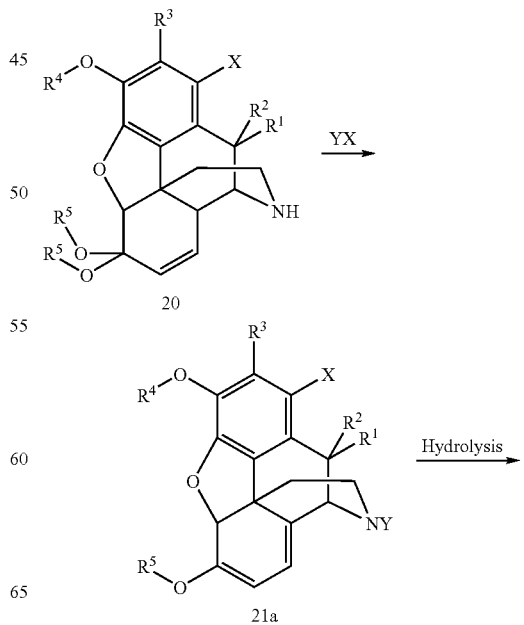

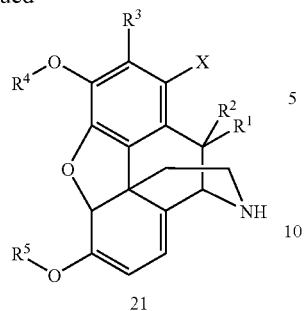

21 wherein:
$R^1$ and $R^2$ are independently chosen from hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group chosen from =O, =S, cycloalkyl ketal, cycloalkyl thiol ketal, and cycloalkyl dithiol ketal;
$R^3$ is chosen from hydrogen, halogen, OH, $NH_2$, CN, $CF_3$, $SO_2R^8$, hydrocarbyl, and substituted hydrocarbyl;
$R^4$ and $R^5$ are independently chosen from —$(CH_2)_nCH_3$, and $CH_3$;
$R^8$ is chosen from hydrocarbyl and substituted hydrocarbyl;
X is halogen;
Y is chosen from an aryl group, a benzyl group, an acyl group, a formyl ester, an alkoxycarbonyl group, a benzyloxycarbonyl group, an alkylamidocarbonyl group, a trialkylsilyl group, an alkylsulfonyl group, and an aryl sulfonyl group; and
YX is chosen from $R_mSiX$, $POX_3$, $(RCO)_2O$, RCOX, $RSO_2X$, and $(RSO_2)_2O$;
m is an integer from 1 to 3; and
n is an integer from 1 to 8.

A further aspect of the invention encompasses a process for the preparation of compound 24s, the process comprising the following reaction scheme:

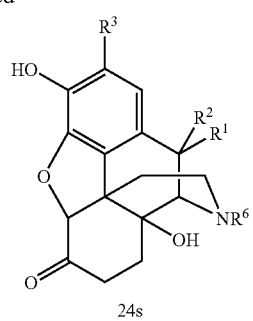

24s wherein:
$R^1$ and $R^2$ are independently chosen from hydrogen, OH, $NH_2$, SH, $CF_3$, hydrocarbyl, substituted hydrocarbyl alkyl ketal, alkyl thiol ketal, and alkyl dithiol ketal, wherein when $R^1$ and $R^2$ are different they form an epimeric pair, and wherein $R^1$ and $R^2$ together may form a group chosen from =O, =S, cycloalkyl ketal, cycloalkyl thiol ketal, and cycloalkyl dithiol ketal;
$R^3$ is chosen from hydrogen, halogen, OH, $NH_2$, CN, $CF_3$, $SO_2R^8$, hydrocarbyl, and substituted hydrocarbyl;
$R^6$ is chosen from hydrogen, an alkyl group, an allyl group, a cycloalkylmethyl group, an aryl group, a benzyl group, and $C(O)_nR^7$;
$R^7$ is chosen from an alkyl group, an aryl group, and a benzyl group;
$R^8$ is chosen from hydrocarbyl and substituted hydrocarbyl;
X is halogen; and
n is an integer from 1 to 2.

Yet another aspect of the invention provides a process for the preparation of compound 24, the process comprising the following reaction scheme:

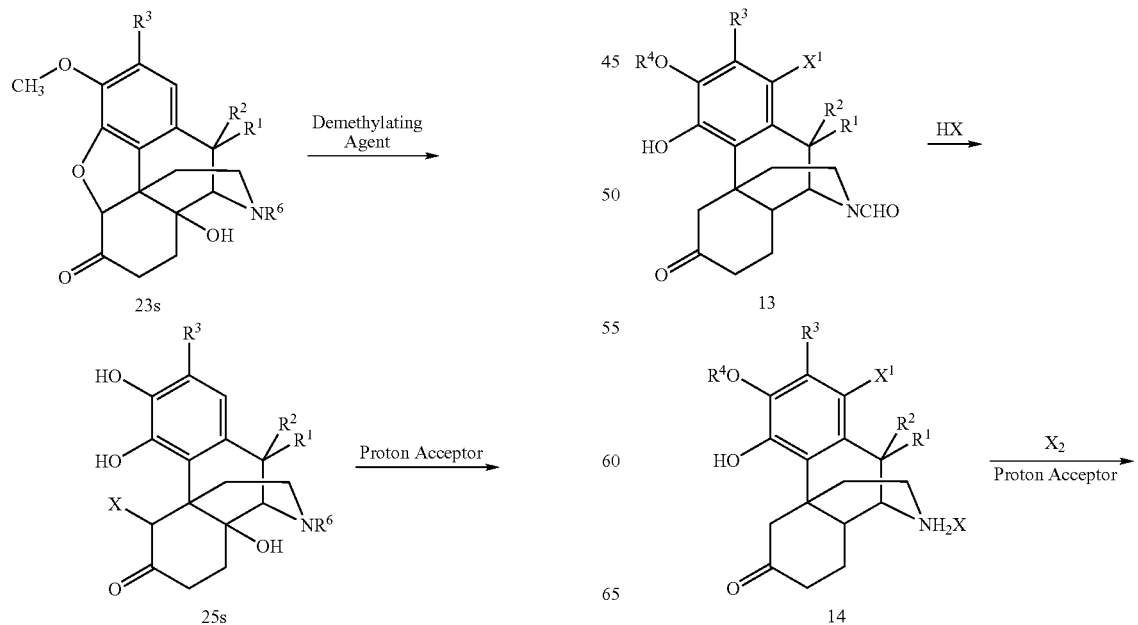

-continued

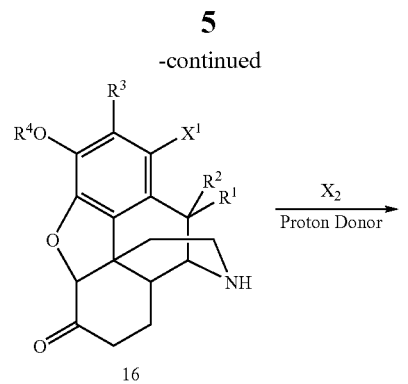
16

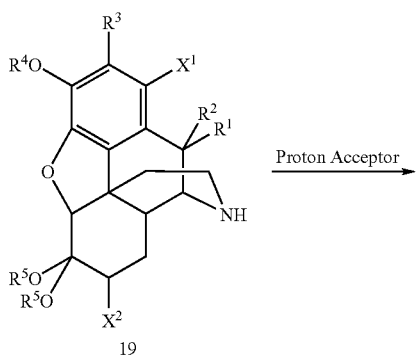
19

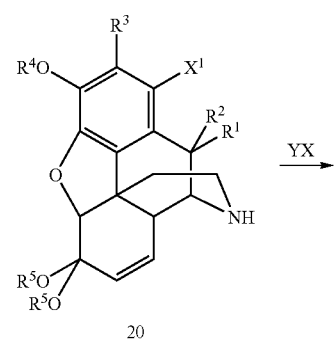
20

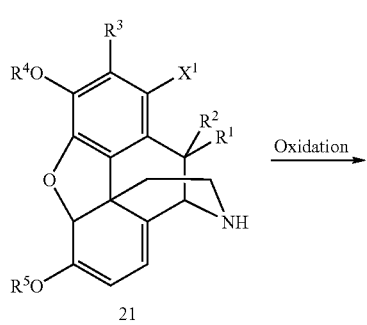
21

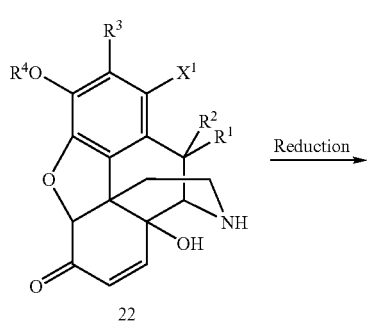
22

-continued

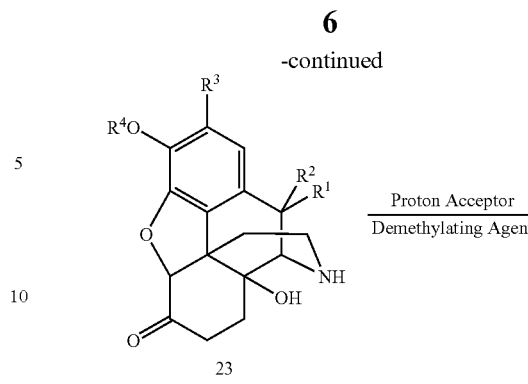
23

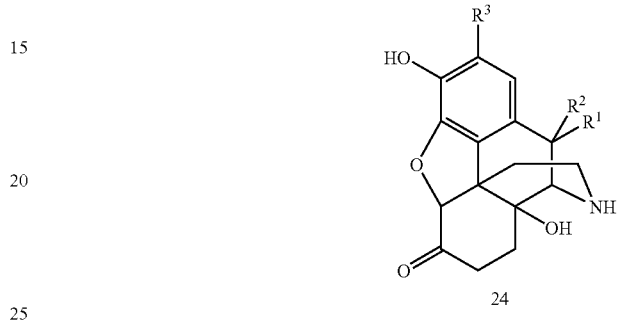
24 wherein:
$R^1$ and $R^2$ are independently chosen from hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group chosen from =O, =S, cycloalkyl ketal, cycloalkyl thiol ketal, and cycloalkyl dithiol ketal;

$R^3$ is chosen from hydrogen, halogen, OH, $NH_2$, CN, $CF_3$, $SO_2R^8$, hydrocarbyl, and substituted hydrocarbyl;

$R^4$ and $R^5$ are independently chosen from —$(CH_2)_nCH_3$ and $CH_3$;

$R^8$ is chosen from hydrocarbyl and substituted hydrocarbyl;

X, $X^1$, and $X^2$ are independently halogen;

YX is chosen from $R_mSiX$, $POX_3$, $(RCO)_2O$, RCOX, $RSO_2X$, and $(RSO_2)_2O$;

m is an integer from 1 to 3; and n is an integer from 1 to 8.

Other aspects and features of the invention are described in more detail below.

DETAILED DESCRIPTION

Processes and compounds for preparing normorphinan compounds, derivatives, and analogs thereof have been discovered. In particular, the compounds and processes may be used for preparing noroxymorphone, noroxymorphone analogs, and noroxymorphone derivatives. The processes of the invention are more efficient, have higher yields, and produce fewer undesirable side-products than currently used synthetic routes.

(I) Normorphinan Compounds

One aspect of the invention encompasses compounds that may be used as intermediates in the preparation of normorphinan related compounds. For purposes of discussion, the ring atoms of a morphinan compound are numbered as

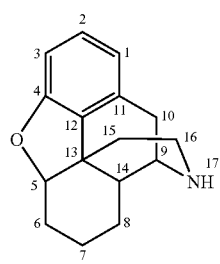

diagrammed below. The core morphinan compound may have four chiral carbons; namely, C-5, C-13, C-14, and C-9.

In one embodiment of the invention, the normorphinan compound

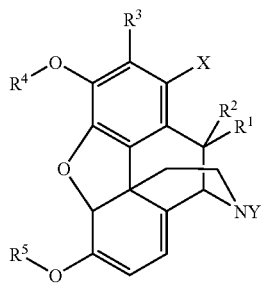

21a comprises Formula 21a:
wherein:
- $R^1$ and $R^2$ are independently selected from the group consisting of hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of =O, =S, cycloalkyl ketal, cycloalkyl thiol ketal, and cycloalkyl dithiol ketal;
- $R^3$ is selected from the group consisting of hydrogen, halogen, OH, $NH_2$, CN, $CF_3$, $SO_2R^8$, hydrocarbyl, and substituted hydrocarbyl;
- $R^4$ and $R^5$ are independently selected from the group consisting of —$(CH_2)_nCH_3$ and $CH_3$;
- $R^8$ is selected from the group consisting hydrocarbyl and substituted hydrocarbyl;
- X is halogen;
- Y is selected from the group consisting of an aryl group, a benzyl group, an acyl group, a formyl ester, an alkoxycarbonyl group, a benzyloxycarbonyl group, an alkylamidocarbonyl group, a trialkylsilyl group, an alkylsulfonyl group, and an aryl sulfonyl group; and
- n is an integer from 1 to 8.

The optical activity, with respect to the rotation of polarized light, of the compound comprising Formula 21a may be (+) or (−). Furthermore, the configuration of the chiral carbons, C-5, C-13, and C-9, respectively, of the compound may be RRR, RRS, RSR, RSS, SRR, SRS, SSR, or SSS, provided that the C-15 and the C-16 carbons are both either on the alpha face or the beta face of the molecule.

In a preferred iteration of this embodiment, $R^1$, $R^2$, and $R^3$ are each hydrogen; $R^4$ and $R^5$ are each $CH_3$; X is bromine; and Y is selected from the group consisting of —$Si(CH_3)_3$, —$COCH_3$, —$CO_2CH_2CH_3$, and —$SO_2CH_3$. Table A presents exemplary compounds comprising Formula 21a.

TABLE A

Exemplary Compounds Comprising Formula 21a.

| Compound Number | Structure |
|---|---|
| A-1 | 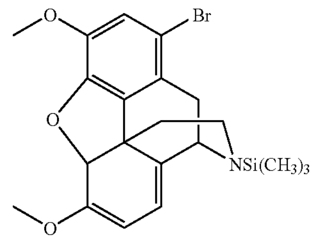 |
| A-2 | 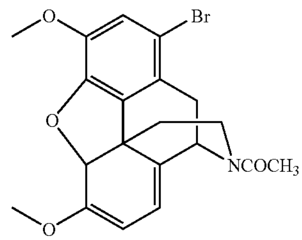 |
| A-3 | 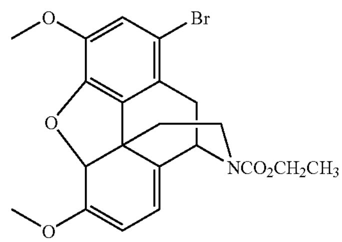 |
| A-4 | 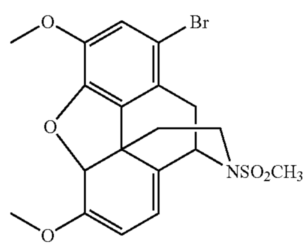 |

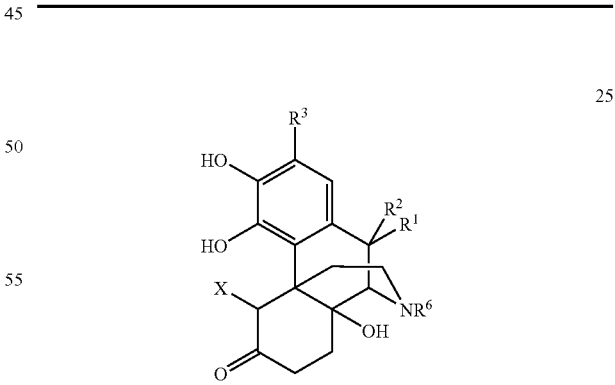

25

In another embodiment, the normorphinan compound comprises Formula 25:
wherein:
- $R^1$ and $R^2$ are independently selected from the group consisting of hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of =O, =S, cycloalkyl ketal, cycloalkyl thiol ketal, and cycloalkyl dithiol ketal;

$R^3$ is selected from the group consisting of hydrogen, halogen, OH, $NH_2$, CN, $CF_3$, $SO_2R^8$, hydrocarbyl, and substituted hydrocarbyl;

$R^6$ is selected from the group consisting of hydrogen, an alkyl group, an allyl group, a cycloalkylmethyl group, an aryl group, a benzyl group, and $C(O)_nR^7$;

$R^7$ is selected from the group consisting of an alkyl group, an aryl group, and a benzyl group;

$R^8$ is selected from the group consisting hydrocarbyl and substituted hydrocarbyl;

X is halogen; and n is an integer from 1 to 2.

The optical activity of the compound comprising Formula 25 may be (+) or (−), and the configuration of the chiral carbons, C-5, C-13, C-14, and C-9, respectively, of the compound may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both either on the alpha face or the beta face of the molecule.

In a preferred iteration of this embodiment, $R^1$, $R^2$, and $R^3$ are each hydrogen; $R^6$ is selected from the group consisting of hydrogen, methyl, —$COCH_3$, and —$CO_2CH_2CH_3$, and X is bromine. Exemplary compounds comprising Formula 25 are presented in Table B.

TABLE B

Exemplary Compounds Comprising Formula 25.

| Compound Number | Structure |
|---|---|
| B-1 | (structure) |
| B-2 | (structure) |
| B-3 | (structure) |
| B-4 | (structure) |

(II) Process for Preparing Compound 24.

Another aspect of the invention provides a process for preparing normorphinans, normorphinan analogs, and derivatives thereof. For the purposes of illustration, Reaction Scheme 1 depicts the preparation of the normorphinan compound comprising Formula 24 according to one aspect of the invention:

Reaction Scheme 1:

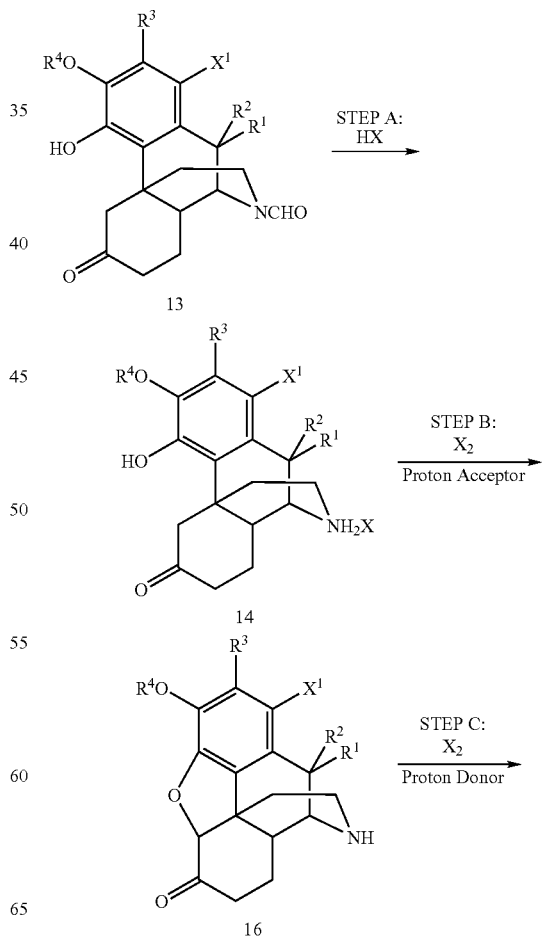

-continued

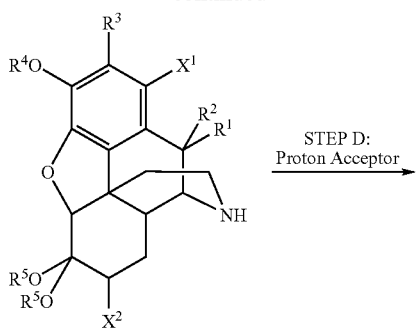

19

STEP D:
Proton Acceptor
→

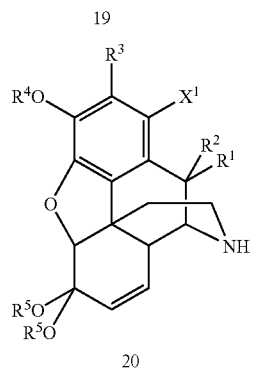

20

STEP E:
YX
→

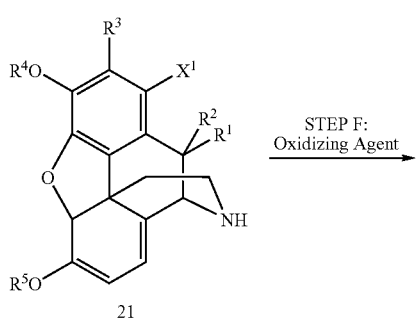

21

STEP F:
Oxidizing Agent
→

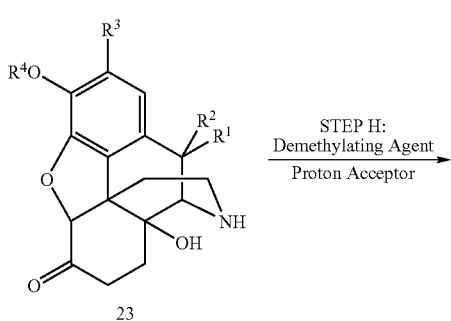

22

STEP G:
Reducing Agent
→

23

STEP H:
Demethylating Agent
Proton Acceptor
→

-continued

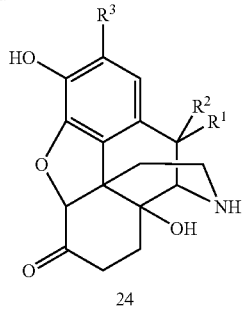

24 wherein:
$R^1$ and $R^2$ are independently selected from the group consisting of hydrogen, OH, $NH_2$, SH, $CF_3$, hydrocarbyl, substituted hydrocarbyl, alkyl ketal, alkyl thiol ketal, and alkyl dithiol ketal, wherein when $R^1$ and $R^2$ are different they form an epimeric pair, and wherein $R^1$ and $R^2$ together may form a group selected from the group consisting of =O, =S, cycloalkyl ketal, cycloalkyl thiol ketal, and cycloalkyl dithiol ketal;

$R^3$ is selected from the group consisting of hydrogen, halogen, OH, $NH_2$, CN, $CF_3$, $SO_2R^8$, hydrocarbyl, and substituted hydrocarbyl;

$R^4$ and $R^5$ are independently selected from the group consisting of $(CH_2)_nCH_3$ and $CH_3$;

$R^8$ is selected from the group consisting hydrocarbyl and substituted hydrocarbyl;

X, $X^1$, and $X^2$ are independently halogen;

YX is selected from the group consisting of $R_mSiX$, $POX_3$, $(RCO)_2O$, RCOX, $RSO_2X$, and $(RSO_2)_2O$;

m is an integer from 1 to 3; and n is an integer from 1 to 8.

In a preferred iteration, the constituents of the reaction comprise:

$R^1$, $R^2$, and $R^3$ are each hydrogen;

$R^4$ and $R^5$ are each $CH_3$;

X is bromine; and

YX is selected from the group consisting of $(CH_3)_3SiCl$, $POCl_3$, $(CH_3CO)_2O$, $CH_3COCl$, $CH_3SO_2Cl$, $CH_3CH_2CO_2Cl$, and $(CH_3SO_2)_2O$.

Reaction Scheme 1 comprises eight steps (A-H), each of which is detailed below.

(a) Step A: Conversion of Compound 13 to Compound 14

In Step A of Reaction Scheme 1, compound 13 is contacted with HX to form compound 14. In general, HX is an acid. Suitable acids include hydrobromic acid, hydrochloric acid, hydroiodic acid, sulfuric acid, methanesulfonic acid, trifluoracetic acid, p-toluenesulfonic acid. In an exemplary embodiment, HX may be hydrobromic acid. The amount of HX contacted with compound 13 can and will vary. Typically, the molar/molar ratio of compound 13 to HX may range from about 1:2 to about 1:20. In a preferred embodiment, the molar/molar ratio of compound 13 to HX may range from about 1:2.5 to about 1:10. In a more preferred embodiment, molar/molar ratio of compound 13 to HX may range from about 1:3 to about 1:5. Contact between compound 13 and HX may proceed slowly over a period of time. For example, in one embodiment, HX may be introduced dropwise over a period of time of at least one hour.

The reaction is generally conducted in the presence of a protic solvent. Non-limiting examples of suitable protic solvents include methanol, ethanol, isopropanol, n-propanol, isobutanol, t-butanol, n-butanol, formic acid, acetic acid, water, and combinations thereof. In an exemplary embodiment, the solvent used in the reaction may be methanol. In general, the weight/weight ratio of solvent to compound 13 may range from about 1:1 to about 100:1. In a preferred embodiment, the weight/weight ratio of solvent to compound 13 may range from about 2:1 to about 25:1. In a more preferred embodiment, the weight/weight ratio of solvent to compound 13 may range from about 5:1 to about 10:1.

In general, the reaction may be conducted at a temperature that ranges from about 20° C. to about 100° C. In a preferred embodiment, the temperature of the reaction may range from about 50° C. to about 90° C. In a more preferred embodiment, the temperature of the reaction may range from about 70° C. to about 85° C. The reaction is preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of compound 13 and a significantly increased amount of compound 14 compared to the amounts of each present at the beginning of the reaction. Typically, the amount of compound 13 remaining in the mixture may be less than about 5%.

The yield of compound 14 may vary. Typically, the yield of compound 14 may be range from about 60% to about 90%. In one embodiment, the yield of compound 14 may range from about 60% to about 70%. In another embodiment, the yield of compound 14 may range from about 70% to about 80%. In still another embodiment, the yield of compound 14 may range from about 80% to about 90%.

(b) Step B: Conversion of Compound 14 to Compound 16

In Step B of Reaction Scheme 1, compound 14 is contacted with $X_2$ and then contacted with a proton acceptor to form compound 16. $X_2$ may be bromine, chlorine, or iodine. In a preferred embodiment, $X_2$ may be bromine ($Br_2$). In one embodiment, the molar/molar ratio of compound 14 to $X_2$ may range from about 1:0.3 to about 1:3. In another embodiment, the molar/molar ratio of compound 14 to $X_2$ may range from about 1:0.5 to about 1:2. In a preferred embodiment, molar/molar ratio of compound 14 to $X_2$ may range from about 1:1 to about 1:1.1. Contact between compound 14 and $X_2$ may proceed slowly over a period of time. In one embodiment, for example, $X_2$ may be introduced dropwise over a period of time of at least 30 minutes. The reaction is generally performed under ambient pressure Compound 14 may be contacted with $X_2$ in the presence of an organic solvent or, more preferably, a mixture of an organic solvent and an acid. Non-limiting examples of suitable organic solvents include benzene, butyl acetate, t-butyl methylether, t-butyl methylketone, chlorobenzene, chloroform, cyclohexane, dichloromethane, dichloroethane, diethyl ether, ethyl acetate, fluorobenzene, heptane, hexane, isopropyl acetate, methyltetrahydrofuran, pentyl acetate, n-propyl acetate, tetrahydrofuran, toluene, and combinations thereof. In a preferred embodiment, the solvent may be chloroform. In an especially preferred embodiment, chloroform may be mixed with an acid, such as acetic acid or propanoic acid. The concentration of the acid in the chloroform may be about 5%, about 10%, about 20%, about 30%, about 40%, about 50%, about 60%, about 70%, about 80% to about 90%. In an exemplary embodiment, the concentration of the acid in the chloroform may be about 50%.

In one embodiment, the weight/weight ratio of solvent to compound 14 may range from about 2:1 to about 100:1. In another embodiment, the weight/weight ratio of solvent to compound 14 may range from about 5:1 to about 80:1. In still another embodiment, the weight/weight ratio of solvent to compound 14 may range from about 10:1 to about 60:1. In a preferred embodiment, the weight/weight ratio of solvent to compound 14 may range from about 35:1 to about 50:1.

The reaction further comprises contact with a proton acceptor. Typically, the proton acceptor will have a pKa of greater than about 12. Non-limiting examples of suitable proton acceptors having this characteristic include hydroxides of alkali metals and alkaline earth metals (such as, for example, NaOH, KOH, and Ca(OH)$_2$ and the like), group 1 salts of carbanions, amides, and hydrides (such as, for example, butyl lithium, sodium amide (NaNH$_2$), sodium hydride (NaH), and the like), alkoxides of alkali metals (such as, for example, potassium butoxide, sodium methoxide, and the like), and a buffer that has a pH greater than about 10 (such as, for example, Na$_3$PO$_4$ or K$_3$PO$_4$). In a preferred embodiment, the proton acceptor may be NaOH, KOH, LiOH, Ca(OH)$_2$, or NaH. In an exemplary embodiment, the proton acceptor may be NaOH.

The molar/molar ratio of compound 14 to proton acceptor may range from about 1:2 to about 1:100. In one embodiment, the molar/molar ratio of compound 14 to proton acceptor may range from about 1:2.5 to about 1:40. In another embodiment, the molar/molar ratio of compound 14 to proton acceptor may range from about 1:3 to about 1:15. In a preferred embodiment, the molar/molar ratio of compound 14 to proton acceptor may range from about 1:3 to about 1:5. Stated another way, the final pH of the reaction mixture may be greater than about pH 10, preferably greater than about pH 12, and more preferably greater than about pH 13. Contact between the reaction mixture and the proton acceptor may occur slowly. In one embodiment, the proton acceptor may be introduced dropwise into the reaction mixture over a period of time. In a preferred embodiment, the reaction mixture may be introduced dropwise into the proton acceptor over a period of time of at least one hour.

The reaction may be performed at a temperature that ranges from about −20° C. to about 40° C. In a preferred embodiment, the reaction may occur at a temperature that ranges from about −1° C. to about 10° C. The reaction is typically performed under ambient pressure.

The reaction is generally allowed to proceed for a sufficient period of time until the reaction is complete, as determined by chromatography (e.g., HPLC). Typically, the amount of compound 14 remaining in the mixture may be less than about 5%.

The yield of compound 16 may range from about 60% to about 90%. In one embodiment, the yield of compound 16 may range from about 60% to about 70%. In another embodiment, the yield of compound 16 may range from about 70% to about 80%. In still another embodiment, the yield of compound 16 may range from about 80% to about 90%.

(c) Step C: Conversion of Compound 16 to Compound 19

Step C of Reaction Scheme 1 comprises contacting compound 16 with $X_2$ and a proton donor to form compound 19. $X_2$ is as defined above in (II)(b). In general, the molar/molar ratio of compound 16 to $X_2$ may range from about 1:0.5 to about 1:2. In a preferred embodiment, the molar/molar ratio of compound 16 to $X_2$ may range from about 1:0.9 to about 1:1.1. Typically, contact between compound 16 and $X_2$ will proceed slowly over a period of time. In one embodiment, for example, $X_2$ may be introduced dropwise over a period of time of at least 30 minutes.

Non-limiting examples of suitable proton donors include $H_2SO_4$, HCl, HBr, HI, $H_3PO_4$, $CF_3SO_3H$, MeSO$_3$H, p-toluenesulfonic acid, HClO$_3$, HBrO$_4$, HIO$_3$, and HIO$_4$. In a preferred embodiment, the proton donor may be $MeSO_3H$ or $H_2SO_4$. In one embodiment, the molar/molar ratio of compound 16 to proton donor may range from about 1:0.5 to about 1:10. In another embodiment the molar/molar ratio of compound 16 to proton donor may range from about 1:0.8 to about 1:5. In a preferred embodiment, the molar/molar ratio of compound 16 to proton donor may range from about 1:1 to about 1:2.

Compound 16 is typically contacted with $X_2$ and the proton donor in the presence of a protic solvent or, more preferably, a mixture of a protic and an organic solvent. Suitable protic solvents are presented above in section (II)(a), and suitable organic solvents are presented above in (II)(b). Preferred solvent systems include a mixture of methanol and trimethylorthoformate, a mixture of ethanol and triethylorthoformate, or a mixture of n-propanol and tripropylorthoformate. In an exemplary embodiment, the solvent system may be a mixture of methanol and trimethylorthoformate. In one embodiment, the weight/weight ratio of solvent to compound 16 may range from about 2:1 to about 100:1. In another embodiment, the weight/weight ratio of solvent to compound 16 may range from about 3:1 to about 30:1. In a preferred embodiment, the weight/weight ratio of solvent to compound 16 may range from about 5:1 to about 10:1.

The reaction may be conducted at a temperature that ranges from about 30° C. to about 100° C. Preferably, the reaction may be conducted at a temperature that ranges from about 40° C. to about 70° C. The reaction is preferably performed under ambient pressure, but optionally may be carried out under reduced pressure.

Typically, the reaction is allowed to proceed for a sufficient period of time until the reaction is complete, as determined by chromatography (e.g., HPLC), and the amount of compound 16 remaining in the mixture may be less than about 5%.

The yield of compound 19 may range from about 60% to about 90%. In one embodiment, the yield of compound 19 may range from about 60% to about 70%. In another embodiment, the yield of compound 19 may range from about 70% to about 80%. In still another embodiment, the yield of compound 19 may range from about 80% to about 90%.

(d) Step D: Conversion of Compound 19 to Compound 20

In Step D of Reaction Scheme 1, compound 19 is contacted with a proton acceptor to form compound 20. Typically, the proton acceptor will have a pKa of greater than about 12. Examples of suitable proton acceptors having this characteristic are presented in (II)(b). Preferred proton donors include butyl lithium, potassium tert-butoxide, sodium tert-butoxide, sodium hydride, sodium amide, and $(Me_3Si)_2NLi$. In an exemplary embodiment, the proton acceptor may be potassium tert-butoxide or sodium tert-butoxide. The molar/molar ratio of compound 19 to proton acceptor can and will vary. In one embodiment, molar/molar ratio of compound 19 to proton acceptor may range from about 1:1 to about 1:10. In another embodiment, molar/molar ratio of compound 19 to proton acceptor may range from about 1:2 to about 1:8. In a preferred embodiment, molar/molar ratio of compound 19 to proton acceptor may range from about 1:4 to about 1:6.

The reaction may be conducted in the presence of an aprotic solvent. Non-limiting examples of aprotic solvents include ether solvents, acetonitrile, benzene, N,N-dimethylformamide, dimethyl sulfoxide, N,N-dimethylpropionamide, 1,3-dimethyl-3,4,5,6-tetrahydro-2(1H)-pyrimidinone, 1,3-dimethyl-2-imidazolidinone, 1,2-dimethoxyethane, bis(2-methoxyethyl)ether, N,N-dimethylacetamide, N-methylpyrrolidinone, ethyl acetate, ethyl formate, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran, 2-methyl tetrahydrofuran, toluene, trichloromethane, and combinations thereof. In a preferred embodiment, the aprotic solvent may be tetrahydrofuran (THF). In one embodiment, the weight/weight ratio of solvent to compound 19 may range from about 2:1 to about 100:1. In another embodiment, the weight/weight ratio of solvent to compound 19 may range from about 2.5:1 to about 20:1. In a preferred embodiment, the weight/weight ratio of solvent to compound 19 may range from about 3:1 to about 8:1.

In one embodiment, the reaction may be conducted at a temperature that ranges from about 20° C. to about 100° C. In another embodiment, the reaction may be conducted at a temperature that ranges from about 40° C. to about 80° C. In a preferred embodiment, the temperature of the reaction may range from about 50° C. to about 70° C. The reaction is preferably performed under ambient pressure, and preferably in an inert atmosphere (e.g., nitrogen or argon).

The reaction is generally allowed to proceed for a sufficient period of time until the reaction is complete, as determined by chromatography (e.g., HPLC). Typically, the amount of compound 19 remaining in the mixture may be less than about 5%.

The yield of compound 20 may range from about 60% to about 90%. In one embodiment, the yield of compound 20 may range from about 60% to about 70%. In another embodiment, the yield of compound 20 may range from about 70% to about 80%. In still another embodiment, the yield of compound 20 may range from about 80% to about 90%.

(e) Step E: Conversion of Compound 20 to Compound 21

Step E of Reaction Scheme 1 comprises contacting compound 20 with reagent YX. Reagent YX is as defined above. In a preferred embodiment, YX may be $(CH_3)_3SiCl$, $CH_3COCl$, $CH_3SO_2Cl$, or $CH_3CH_2CO_2Cl$, The molar/molar ratio of compound 20 to YX may vary. In one embodiment, the molar/molar ratio of compound 20 to YX may range from about 1:1 to about 1:50. In another embodiment, the molar/molar ratio of compound 20 to YX may range from about 1:1.2 to about 1:15. In a preferred embodiment, the molar/molar ratio of compound 20 to YX may range from about 1:1.5 to about 1:5.

The reaction may be conducted in the presence of an aprotic solvent. Examples of suitable aprotic solvents are presented above in (II)(d). In a preferred embodiment, the aprotic solvent may be acetonitrile. In one embodiment, the weight/weight ratio of solvent to compound 20 may range about 2:1 to about 50:1. In another embodiment, the weight/weight ratio of solvent to compound 20 may range about 3:1 to about 40:1. In a preferred embodiment, the weigh/weight ratio of solvent to compound 20 may range from about 5:1 to about 20:1. Contact between compound 20 and reagent YX may be preformed at a temperature that ranges from about 0° C. to about 80° C. Preferably, contact between compound 20 and reagent YX may be preformed at a temperature that ranges from about 15° C. to about 35° C. The reaction is preferably performed under ambient pressure.

The reaction further comprises hydrolysis in the presence of an aqueous solution to form compound 21. In a preferred embodiment, the aqueous solution may be water or a solution of ammonium hydroxide. In general, the pH of the aqueous solution may range from about pH 7 to about pH 12, or more preferably from about pH 8 to about pH 10. The weight/weight ratio of compound 20 to aqueous solution may range from 1:1 to about 1:50, or more preferably from about 1:2 to about 1:8. The hydrolysis may be conducted at a temperature that ranges from about 0° C. to about 100° C., or more preferably from about 10° C. to about 50° C. The reaction is preferably performed under ambient pressure.

The reaction generally is allowed to proceed for a sufficient period of time until the reaction is complete, as determined by chromatography (e.g., HPLC). Typically, the amount of compound 20 remaining in the mixture may be less than about 5%.

The yield of compound 21 may range from about 60% to about 90%. In one embodiment, the yield of compound 21 may range from about 60% to about 70%. In another embodiment, the yield of compound 21 may range from about 70% to about 80%. In still another embodiment, the yield of compound 21 may range from about 80% to about 90%.

(f) Step F: Conversion of Compound 21 to Compound 22

In Step F of Reaction Scheme 1, compound 21 is contacted with an oxidizing agent to form compound 22. The oxidizing agent may be selected from the group consisting of $R^zCO_3H$, $R^zCO_2H/H_2O_2$, and $R^zCO_2H$/other oxidant, wherein $R^z$ is selected from the group consisting of alkyl, substituted alkyl, aryl, and substituted aryl. In a preferred embodiment the oxidizing agent may be a peroxy acid, such as peracetic acid or 3-chloroperoxybenzoic acid. In one embodiment, the molar/molar ratio of compound 21 to oxidizing agent may range from about 1:0.5 to about 1:3. In another embodiment, the molar/molar ratio of compound 21 to oxidizing agent may range from about 1:0.8 to about 1:2. In a preferred embodiment, the molar/molar ratio of compound 21 to oxidizing agent may range from about 1:1 to about 1:1.2.

The reaction may be conducted in the presence of a protic solvent. Suitable protic solvents are presented above in (II) (a). In a preferred embodiment, the protic solvent may be a combination of water and acetic acid. The solvent system may alternatively, or additionally, comprise other protic solvents such as alcohol or other water-miscible solvent; thus, for example, the protic solvent may be water, a water/alcohol mixture, or a water/water-miscible solvent mixture. Representative alcohols for the water/alcohol mixture include, for example, methanol, ethanol, t-butyl alcohol, n-propyl alcohol, n-butyl alcohol, and combinations thereof. Other water-miscible solvents for the water/water-miscible solvent mixture include, for example, acetonitrile, N,N-dimethylformamide, 1-methyl-2-pyrrolidinone, N,N-dimethylacetamide, and combinations thereof. The weight/weight ratio of solvent to compound 21 may range from about 2:1 to about 50:1. Preferably, the weight/weight ratio of solvent to compound 21 range from about 2:1 to about 5:1.

The reaction may be conducted at a temperature that ranges from about −5° C. to about 50° C. In a preferred embodiment, the temperature of the reaction may range from about 5° C. to about 35° C. The reaction is preferably performed under ambient pressure.

The reaction generally is allowed to proceed for a sufficient period of time until the reaction is complete, as determined by chromatography (e.g., HPLC). Typically, the amount of compound 21 remaining in the mixture may be less than about 5%.

The yield of compound 22 may range from about 60% to about 90%. In one embodiment, the yield of compound 22 may range from about 60% to about 70%. In another embodiment, the yield of compound 22 may range from about 70% to about 80%. In still another embodiment, the yield of compound 22 may range from about 80% to about 90%.

(g) Step G: Conversion of Compound 22 to Compound 23

Step G of Reaction Scheme 1 comprises the reduction of compound 22 to form compound 23. For this, compound 22 is contacted with a reducing agent. A variety of reducing approaches may be employed including, for example, chemical reduction, catalytic reduction, and the like. Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. In a preferred embodiment, compound 22 is reduced catalytically by palladium on carbon (Pd—C) under pressurized hydrogen. The molar/molar ratio of compound 22 to reducing agent may range from about 10,000:1 to about 100:1, or more preferably from about 5000:1 to about 1000:1.

The reaction may be conducted in the presence of a protic solvent, such as, for example, a combination of water and acetic acid. Other suitable protic or water-miscible solvents are presented above in (II)(f). In one embodiment, the weight/weight ratio of solvent to compound 22 may range from about 2:1 to about 50:1. In a preferred embodiment, the weight/weight ratio of solvent to compound 22 may range from about 2:1 to about 5:1.

The reaction may be conducted at a temperature that ranges from about 20° C. to about 110° C. In a preferred embodiment, the temperature of the reaction may range from about 35° C. to about 85° C. The reaction may be performed under hydrogen. The hydrogen pressure may range from about 1 psi to about 200 psi, and more preferably from about 20 psi to about 80 psi.

The reaction generally is allowed to proceed for a sufficient period of time until the reaction is complete, as determined by chromatography (e.g., HPLC). Typically, the amount of compound 22 remaining in the mixture may be less than about 5%.

The yield of compound 23 may range from about 60% to about 90%. In one embodiment, the yield of compound 23 may range from about 60% to about 70%. In another embodiment, the yield of compound 23 may range from about 70% to about 80%. In still another embodiment, the yield of compound 23 may range from about 80% to about 90%.

(h) Step H: Conversion of Compound 23 to Compound 24

In Step H of Reaction Scheme 1, compound 23 is first contacted with a demethylating agent and then contacted with a proton acceptor to form compound 24. Non-limiting examples of suitable demethylating agents include $BBr_3$, $BCl_3$, HBr, methionine/$MeSO_3H$, aluminum bromide, and aluminum chloride ethanethiol. In a preferred embodiment, the demethylating agent may be $BBr_3$ or HBr. The amount of demethylating agent contacted with compound 23 may vary. In one embodiment, the molar/molar ratio of compound 23 to demethylating agent may range from about 1:5 to about 1:20. In another embodiment, the molar/molar ratio of compound 23 to demethylating agent may range from about 1:3 to about 1:12. In a preferred embodiment, the molar/molar ratio of compound 23 to demethylating agent may range from about 1:2 to about 1:4.

Contact with the demethylating agent may be conducted in the presence of an organic solvent. Examples of suitable organic solvents are presented above in (II)(b). In a preferred embodiment, the organic solvent may be chloroform. In general, the weight/weight ratio of solvent to compound 23 may range from about 2:1 to about 50:1. Preferably, the weight/weight ratio of solvent to compound 23 range from about 5:1 to about 15:1. The reaction may be conducted at a temperature that ranges from about −20° C. to about 120° C. In embodiments in which the demethylating agent is BBr$_3$, the temperature of the reaction may range from about 0° C. to about 30° C. And in embodiments in which the demethylating agent is HBr, the temperature of the reaction may range from about 90° C. to about 105° C. The reaction is preferably performed under ambient pressure.

The reaction further comprises contact with a proton acceptor. For this, a protic solvent may be added to the reaction mixture, whereby organic and aqueous phases are formed. Suitable protic solvents are presented above in (II)(a). In a preferred embodiment, the protic solvent may be water. In general, the weight/weight ratio of protic solvent to compound 23 may range from about 3:1 to about 50:1, or more preferably from about 5:1 to about 20:1. The proton acceptor may be added to the aqueous phase of the reaction mixture such that pH of the mixture ranges from about pH 7 to about pH 12, or more preferably, from about pH 8 to about pH 10. In general, the proton acceptor will generally have a pKa of greater than about 8. Examples of suitable proton acceptors include weak bases such as NH$_4$OH, NaHCO$_3$, KHCO$_3$, and Na$_2$CO$_3$, as well as proton acceptors presented above in (II)(b). In a preferred embodiment, the proton acceptor may be sodium hydroxide (NaOH). The molar/molar ratio of compound 23 to proton acceptor may range from about 1:5 to about 1:100, or more preferably from about 1:15 to about 1:30. Contact with the proton acceptor may be conducted at a temperature that ranges from about 0° C. to about 110° C., or more preferably from about 20° C. to about 80° C. The reaction is preferably performed under ambient pressure. Typically, the reaction is allowed to proceed for a sufficient period of time until the reaction is complete, as determined by chromatography (e.g., HPLC).

The yield of compound 24 may range from about 60% to about 90%. In one embodiment, the yield of compound 24 may range from about 60% to about 70%. In another embodiment, the yield of compound 24 may range from about 70% to about 80%. In still another embodiment, the yield of compound 24 may range from about 80% to about 90%.

(III) Process for Preparing Compound 21a and Compound 21

A further aspect of the invention provides a process for preparing compound 21, wherein an intermediate compound comprising Formula 21a is formed. The process comprises contacting compound 20 with YX to form compound 21a, which is then hydrolyzed to form compound 21. For the purposes of illustration, Reaction Scheme 2 depicts the preparation of compound 21a and compound 21:

Reaction Scheme 2:

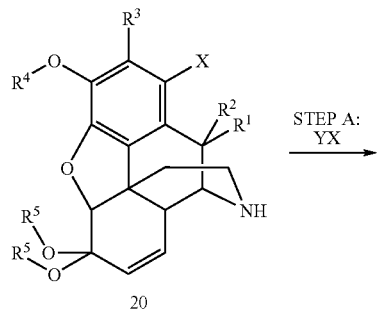

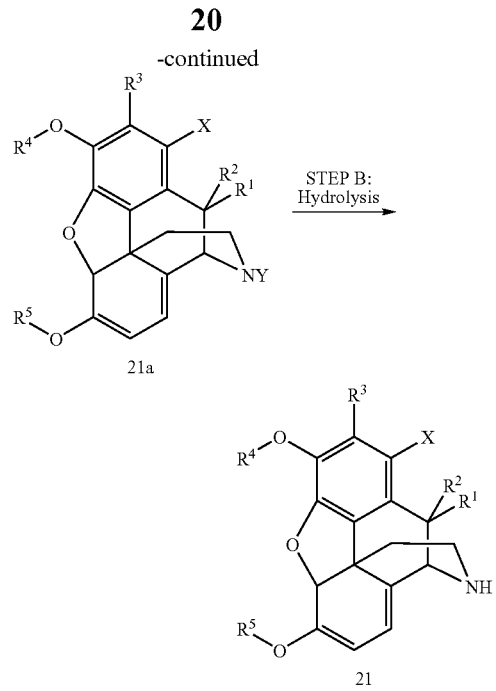

wherein:
R$^1$ and R$^2$ are independently selected from the group consisting of hydrogen, OH, NH$_2$, SH, CF$_3$, hydrocarbyl, substituted hydrocarbyl, alkyl ketal, alkyl thiol ketal, and alkyl dithiol ketal, wherein when R$^1$ and R$^2$ are different they form an epimeric pair, and wherein R$^1$ and R$^2$ together may form a group selected from the group consisting of =O, =S, cycloalkyl ketal, cycloalkyl thiol ketal, and cycloalkyl dithiol ketal;
R$^3$ is selected from the group consisting of hydrogen, halogen, OH, NH$_2$, CN, CF$_3$, SO$_2$R$^8$, hydrocarbyl, and substituted hydrocarbyl;
R$^4$ and R$^5$ are independently selected from the group consisting of —(CH$_2$)$_n$CH$_3$, and CH$_3$;
R$^8$ is selected from the group consisting hydrocarbyl and substituted hydrocarbyl;
X is halogen;
Y is selected from the group consisting of an aryl group, a benzyl group, an acyl group, a formyl ester, an alkoxycarbonyl group, a benzyloxycarbonyl group, an alkylamidocarbonyl group, a trialkylsilyl group, an alkylsulfonyl group, and an aryl sulfonyl group;
YX is selected from the group consisting of R$_m$SiX, POX$_3$, (RCO)$_2$O, RCOX, RSO$_2$X, and (RSO$_2$)$_2$O;
m is an integer from 1 to 3; and
n is an integer from 1 to 8.

In a preferred iteration of this embodiment, the constituents of the reaction comprise:
R$^1$, R$^2$, and R$^3$ are each hydrogen;
R$^4$ and R$^5$ are each CH$^3$; and
YX is selected from the group consisting of (CH$_3$)$_3$SiCl, POCl$_3$, (CH$_3$CO)$_2$O, CH$_3$COCl, CH$_3$SO$_2$Cl, CH$_3$CH$_2$CO$_2$Cl, and (CH$_3$SO$_2$)$_2$O;
X is bromine; and
Y is selected from the group consisting of —Si(CH$_3$)$_3$, —COCH$_3$, —CO$_2$CH$_2$CH$_3$, and —SO$_2$CH$_3$.

(a) Step A: Conversion of Compound 20 to Compound 21a

In Step A of Reaction Scheme 2, compound 20 is contacted with YX to form compound 21a. Reagent YX is as defined above. In a preferred embodiment, YX may be (CH$_3$)$_3$SiCl, CH$_3$COCl, CH$_3$SO$_2$Cl, or CH$_3$CH$_2$CO$_2$Cl. In one exemplary embodiment, YX may be (CH$_3$)$_3$SiCl, and Y may be —Si(CH$_3$)$_3$. In another exemplary embodiment, YX may be CH$_3$COCl, and Y may be —COCH$_3$. In a further exemplary embodiment, YX may be CH$_3$SO$_2$Cl, and Y may be —SO$_2$CH$_3$. In yet another exemplary embodiment, YX may be CH$_3$CH$_2$CO$_2$Cl, and Y may be —CO$_2$CH$_2$CH$_3$. The molar/molar ratio of compound 20 to YX can and will vary. In one embodiment, the molar/molar ratio of compound 20 to YX may range from about 1:1 to about 1.50. In another embodiment, the molar/molar ratio of compound 20 to YX may range from about 1:1.2 to about 1:15. In a preferred embodiment, the molar/molar ratio of compound 20 to YX may range from about 1:1.5 to about 1:5.

The reaction may be conducted in the presence of an aprotic solvent. Examples of suitable aprotic solvents are presented above in (II)(d). In a preferred embodiment, the aprotic solvent is acetonitrile. In one embodiment, the weight/weight ratio of solvent to compound 20 may range about 2:1 to about 50:1. In another embodiment, the weight/weight ratio of solvent to compound 20 may range about 3:1 to about 40:1. In a preferred embodiment, the weight/weight ratio of solvent to compound 20 may range from about 5:1 to about 20:1.

The temperature of the reaction may range from about 0° C. to about 80° C. In a preferred embodiment, the temperature of the reaction may range from about 15° C. to about 35° C. The reaction is preferably performed under ambient pressure.

Typically, the reaction is allowed to proceed for a sufficient period of time until the reaction is complete, as determined by chromatography (e.g., HPLC), and the amount of compound 20 remaining in the mixture may be less than about 5%.

The yield of compound 21a may range from about 60% to about 90%. In one embodiment, the yield of compound 21a may range from about 60% to about 70%. In another embodiment, the yield of compound 21a may range from about 70% to about 80%. In still another embodiment, the yield of compound 21a may range from about 80% to about 90%.

(b) Step B: Conversion of Compound 21a to Compound 21

Step B of Reaction Scheme 2 comprises hydrolysis of compound 21a to form compound 21. Specifically, compound 21a is deprotected by reaction with an aqueous solution to form compound 21. In a preferred embodiment, the aqueous solution may be water or a solution of ammonium hydroxide. In general, the pH of the aqueous solution may range from about pH 7 to about pH 12, or more preferably from about pH 8 to about pH 10. The weight/weight ratio of compound 21a to aqueous solution may range from 1:1 to about 1:50, preferably from about 1:1.5 to about 1:20, or more preferably from about 1:2 to about 1:8.

The reaction may be conducted at a temperature that ranges from about 0° C. to about 100° C. In a preferred embodiment, the temperature of the reaction may range from about 10° C. to about 50° C. The reaction is preferably performed under ambient pressure. The reaction generally is allowed to proceed for a sufficient period of time until the reaction is complete, as determined by chromatography (e.g., HPLC). Typically, the amount of compound 21a remaining in the mixture may be less than about 5%.

The yield of compound 21 may range from about 60% to about 90%. In one embodiment, the yield of compound 21 may range from about 60% to about 70%. In another embodiment, the yield of compound 21 may range from about 70% to about 80%. In still another embodiment, the yield of compound 21 may range from about 80% to about 90%.

(IV) Process for the Preparation of Compound 25s and Compound 24s

Still another aspect of the invention encompasses a process for the preparation of compound 24s, wherein an intermediate compound comprising Formula 25s is formed. The process comprises contacting compound 23s with a demethylating agent to form compound 25s, which is then contacted with a proton acceptor to form compound 24s, as depicted in Reaction Scheme 3:

Reaction Scheme 3:

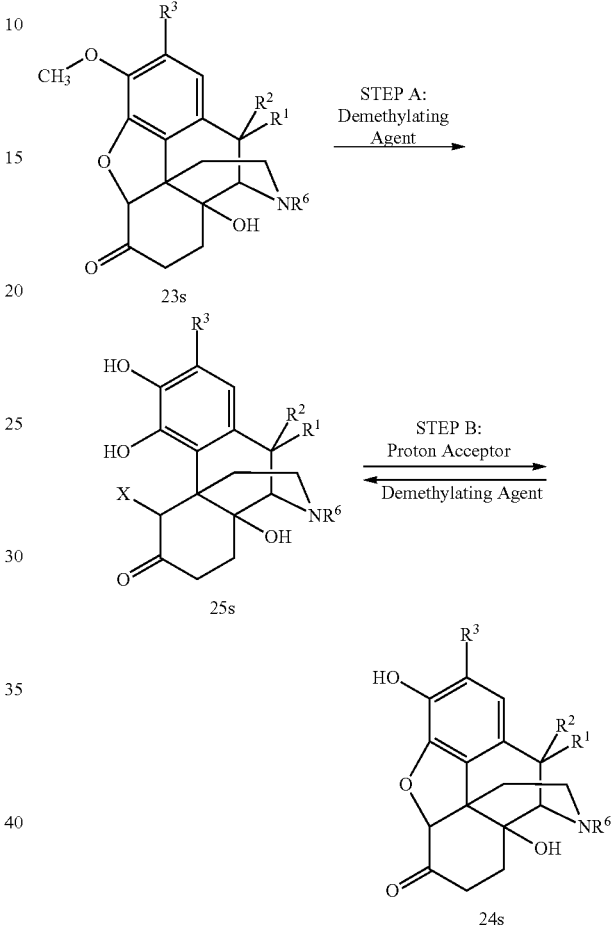

wherein:
R$^1$ and R$^2$ are independently selected from the group consisting of hydrogen, OH, NH$_2$, SH, CF$_3$, hydrocarbyl, substituted hydrocarbyl, alkyl ketal, alkyl thiol ketal, and alkyl dithiol ketal, wherein when R$^1$ and R$^2$ are different they form an epimeric pair, and wherein R$^1$ and R$^2$ together may form a group selected from the group consisting of =O, =S, cycloalkyl ketal, cycloalkyl thiol ketal, and cycloalkyl dithiol ketal;
R$^3$ is selected from the group consisting of hydrogen, halogen, OH, NH$_2$, CN, CF$_3$, SO$_2$R$^8$, hydrocarbyl, and substituted hydrocarbyl;
R$^6$ is selected from the group consisting of hydrogen, an alkyl group, a cycloalkylmethyl group, an aryl group, a benzyl group, and C(O)$_n$R$^7$;
R$^7$ is selected from the group consisting of an alkyl group, an aryl group, and a benzyl group;
R$^8$ is selected from the group consisting hydrocarbyl and substituted hydrocarbyl;
X is halogen; and
n is an integer from 1 to 2.

In a preferred iteration, the constituents of the reaction comprise:

$R^1$, $R^2$, and $R^3$ are each hydrogen;

$R^6$ is selected from the group consisting of hydrogen, $CH_3$, —$COCH_3$, and —$CO_2CH_2CH_3$; and X is bromine.

(a) Step A: Conversion of Compound 23s to Compound 25s

In Step A of Reaction Scheme 3, compound 23s is contacted with a demethylating agent to form compound 25s. Non-limiting examples of suitable demethylating agents include $BBr_3$, $BCl_3$, HBr, methionine/$MeSO_3H$, aluminum bromide, and aluminum chloride ethanethiol. In a preferred embodiment, the demethylating agent may be BBr3 or HBr. In general, the molar/molar ratio of compound 23 to demethylating agent may range from about 1:5 to about 1:20. In a preferred embodiment, the molar/molar ratio of compound 23 to demethylating agent may range from about 1:3 to about 1:12. In an exemplary embodiment, the molar/molar ratio of compound 23 to demethylating agent may range from about 1:2 to about 1:4.

Contact with the demethylating agent may be conducted in the presence of an organic solvent. Examples of suitable organic solvents are presented above in (II)(b). In a preferred embodiment, the organic solvent may be chloroform. Typically, the weight/weight ratio of solvent to compound 23 will range from about 2:1 to about 50:1. In a preferred embodiment, the weight/weight ratio of solvent to compound 23 range from about 5:1 to about 15:1.

In general, the reaction may be conducted at a temperature that ranges from about −20° C. to about 120° C. In embodiments in which the demethylating agent is $BBr_3$, the temperature of the reaction may range from about 0° C. to about 30° C. And in embodiments in which the demethylating agent is HBr, the temperature of the reaction may range from about 90° C. to about 105° C. The reaction is preferably performed under ambient pressure.

The reaction generally is allowed to proceed for a sufficient period of time until the reaction is complete, as determined by chromatography (e.g., HPLC). Typically, the amount of compound 23s remaining in the mixture may be less than about 5%.

The yield of compound 25s may range from about 60% to about 90%. In one embodiment, the yield of compound 25s may range from about 60% to about 70%. In another embodiment, the yield of compound 25s may range from about 70% to about 80%. In still another embodiments the yield of compound 25s may range from about 80% to about 90%.

(b) Step B forward: Conversion of Compound 25s to Compound 24s

Step B of Reaction Scheme 3 comprises contacting compound 25s with a proton acceptor to form compound 24s. Typically, the proton acceptor will generally have a pKa of greater than about 8. Examples of suitable proton acceptors include weak bases such as $NH_4OH$, $NaHCO_3$, $KHCO_3$, and $Na_2CO_3$, as well as proton acceptors presented above in (II)(b). In a preferred embodiment, the proton acceptor may be sodium hydroxide (NaOH). Stated another way, upon addition of the proton acceptor, the pH of reaction mixture may range from about pH 7 to about pH 12, or more preferably, from about pH 8 to about pH 10. In one embodiment, the molar/molar ratio of compound 25s to proton acceptor may range from about 1:5 to about 1:100. In another embodiment the molar/molar ratio of compound 25s to proton acceptor may range from about 1:10 to about 1:50. In a preferred embodiment, the molar/molar ratio of compound 25s to proton acceptor range from about 1:15 to about 1:30.

The reaction may be performed in the presence of a protic solvent. Suitable protic solvents are presented above in (II)(a). In a preferred embodiment, the protic solvent may be water. The weight/weight ratio of protic solvent to compound 25s may range from about 3:1 to about 50:1, or more preferably from about 5:1 to about 20:1.

The temperature of the reaction may range from about 0° C. to about 110° C. In a preferred embodiment, the temperature of the reaction may range from about 20° C. to about 80° C. The reaction is preferably performed under ambient pressure.

The reaction generally is allowed to proceed for a sufficient period of time until the reaction is complete, as determined by chromatography (e.g., HPLC). Typically, the amount of compound 25s remaining in the mixture may be less than about 5%.

The yield of compound 24s may range from about 60% to about 90%. In one embodiment, the yield of compound 24s may range from about 60% to about 70%. In another embodiment, the yield of compound 24s may range from about 70% to about 80%. In still another embodiment, the yield of compound 24s may range from about 80% to about 90%.

(c) Step B Reverse: Conversion of Compound 24s to Compound 25s

Step B of Reaction Scheme 3 also comprises the conversion of compound 24s to compound 25s. For this, compound 24s is contacted with a demethylating agent to form compound 25s. Examples of suitable demethylating agents are presented above in (IV)(a). The molar/molar ratio of compound 24s to demethylating agent may range from about 1:5 to about 1:20, preferably from about 1:3 to about 1:12, or more preferably from about 1:2 to about 1:4. Contact with the demethylating agent may be conducted in the presence of an organic solvent. Examples of suitable organic solvents are presented above in (II)(b). In a preferred embodiment, the organic solvent may be chloroform. The weight/weight ratio of solvent to compound 24s will range from about 2:1 to about 50:1, or preferably from about 5:1 to about 15:1.

The reaction may be conducted at a temperature that ranges from about −20° C. to about 120° C. The reaction is preferably performed under ambient pressure. The reaction generally is allowed to proceed for a sufficient period of time until the reaction is complete, as determined by chromatography (e.g., HPLC). Typically, the amount of compound 24s remaining in the mixture may be less than about 5%.

The yield of compound 25s may range from about 60% to about 90%. In one embodiment, the yield of compound 25s may range from about 60% to about 70%. In another embodiment, the yield of compound 25s may range from about 70% to about 80%. In still another embodiment, the yield of compound 25s may range from about 80% to about 90%.

(V) Compounds Prepared from Compound 24

Compounds corresponding to compound 24 may be end products themselves, or intermediates that may be further derivatized in one or more steps to yield further morphinan intermediates or end products. By way of non-limiting example, one or more compounds corresponding to compound 24 may be used in processes to produce a compound selected from the group consisting of nalbuphine, nalmefene, naloxone, naltrexone, naltrexone methobromide, 3-O-methyl naltrexone, α- or β-naltrexol, α- or β-naloxol, α- or β-naltrexamine, and the salts, intermediates, and analogs thereof. General reaction schemes for the preparation of such commercially valuable morphinans are disclosed, among other places, in U.S. Pat. No. 4,368,326 to Rice, the entire disclosure of which is hereby incorporated by reference herein.

Additionally, in some embodiments, the 6-ketone of compound 24 may be reduced to 6-α-OH, 6-β-OH, 6-α-NH$_2$, or 6-β-NH$_2$.

DEFINITIONS

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R^1$, $R^1O-$, $R^1R^2N-$, or $R^1S-$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like. "Allyl" refers to an alkenyl group comprising a vinyl group attached to a methylene group.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl (such as a benzyl group) are the more preferred aryl groups.

The terms "halogen" or "halo" as used herein alone or as part of another group refer to chlorine, bromine, fluorine, and iodine. The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

EXAMPLES

The following examples illustrate the synthesis of noroxymorphone, as depicted in the following reaction scheme:

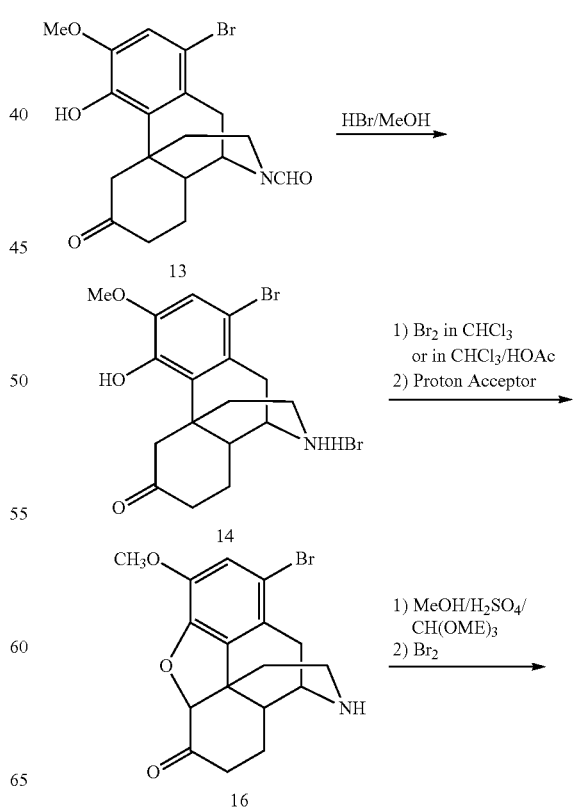

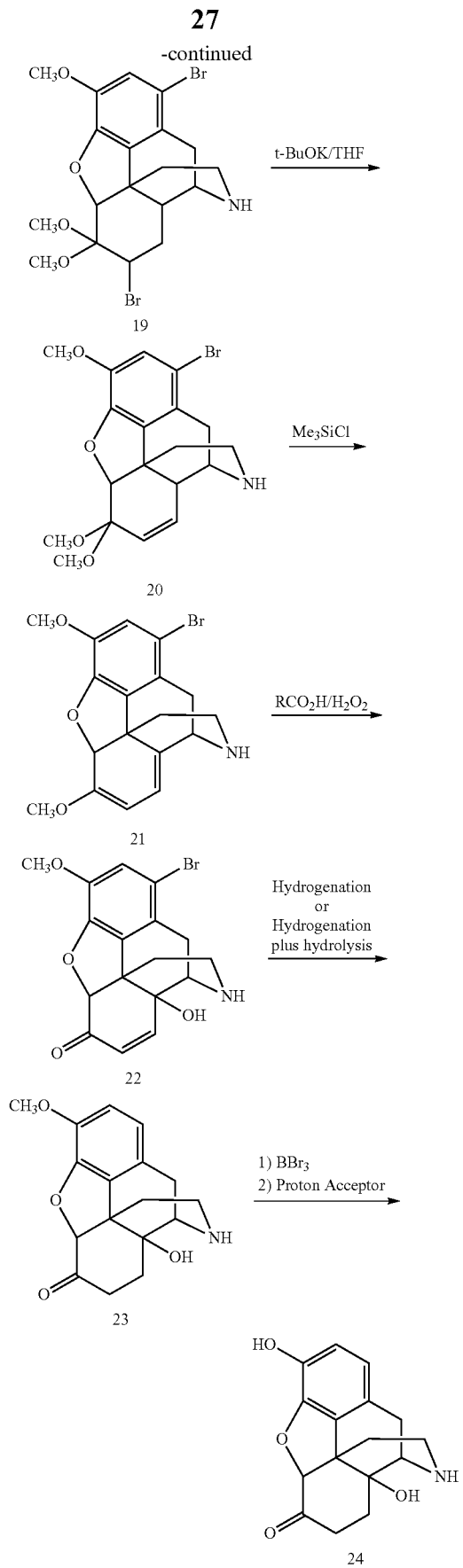

Example 1

Synthesis of Compound 14 from Compound 13

Compound 13 (107 g; assayed 82%; 88 g actual; 0.224 mole) and methanol (MeOH) (850 mL) were combined and stirred for ~15 minutes. After filtration to remove the insoluble materials, the solid was washed with methanol (200 mL). The combined filtrate and wash were placed in a 2 L flask under a nitrogen atmosphere and 48% hydrobromic acid (HBr) (88 mL) was slowly added while keeping the temperature below 40° C. The reaction mixture was distilled until a pot temperature of 75° C. was attained. The mixture was refluxed for 3-5 hours. The reaction was determined to be complete when HPLC analysis indicated less than 2% of compound 13 remained. Water (850 mL) was added and the mixture was heated to ~60-70° C. until all the solids dissolved. The mixture was cooled to 55-60° C. and chloroform was added (150 mL). The phases were stirred, allowed to settle, and then separated. To the aqueous phase was added chloroform (50 mL), the phases were stirred, allowed to settle, and then separated. Water (82 mL), methanol (18 mL), and 5 drops of 48% HBr were added to the combined chloroform extracts. The phases were stirred, allowed to settle, and then separated. The chloroform phases contained ~8 gm/L of compound 14. The aqueous phases from the last two extractions were combined and cooled to 0-10° C. with stirring for 1-2 hours. The solids were separated by filtration and the cake was washed with water (100 mL). The solid was dried at 60° C. under partial vacuum with a nitrogen sweep. The drying time was ~72 hours. The combined liquors contained ~8 g/L of compound 14. Table 1 presents the results from two reactions.

TABLE 1

Synthesis of Compound 14.

| Expt # | Weight Yield | Percent Yield | W/W Assay |
|---|---|---|---|
| 1 | 78 g | 78% | 96.9% |
| 2 | 73 g | 73% | 95.0% |

Example 1a

Another Synthesis of Compound 14 from Compound 13

Compound 13 (73.2 g; 0.19 moles; 96 w/w %) and anhydrous methanol (250 mL) were added to a three-necked round bottom flask equipped with a mechanical stirrer. The mixture was cooled to 5° C. and 48% hydrobromic acid (150.2 g; 1.86 moles) was added dropwise over a period of an hour. The addition funnel was removed and replaced with a short place distillation set-up. The reaction was warmed slowly to reflux (set point 85° C., pot temperature 75° C.). The reaction was refluxed for 4 hours and 125 mL of solvent was distilled off. Liquid chromatography revealed that approximately 1% of compound 13 remained.

The reaction was cooled to 50° C. and 125 mL of distilled water was added. After stirring for 5 min, the aqueous phase was extracted with chloroform (3×100 mL) at a temperature between 40° C. and 50° C. The organic phase was discarded, and 3 ml of 48% HBr was added to the aqueous phase. The mixture was stirred until it reached room temperature, and then it was cooled to 0° C. After standing at 0° C. for 2 hours, crystals formed. The crystals were removed by filtration, washed with 25 mL of cold water, and dried. The filtrate was cooled again to 0° C., the crystals were filtered, and washed with water. This process was repeated two more times, for a total of four crops of crystals. Weight of compound 14, 55.6 g; yield, 81.8%; assay, 97 w/w %.

Example 2

Synthesis of Compound 16 from Compound 14

Compound 14 HBr salt (50 g; assayed ~95%; 47.5 g actual; 0.16 mole), chloroform ($CHCl_3$) (1 L), and 48% HBr (3.5 mL) were added to a glass reactor. The mixture was stirred and cooled to −45 to −55° C. Bromine (20.2 g; 0.126 mole) was diluted to 500 mL with chloroform, and the solution was placed in an addition funnel. Bromine solution (450 mL) was added to the reaction mixture over a 30 minute period at −50° C. HPLC indicated that 9.8% of unreacted compound 14 remained. Additional bromine solution (30 mL) was added to the reaction mixture. HPLC indicated that 2.9% of unreacted compound 14 remained, but the over bromination products were growing. The reaction was allowed to warm to ~10° C., and 4 N sodium hydroxide (1 L) was added. The mixture was stirred for 15 minutes, the phases were allowed to settle, and then separated. 1N sodium hydroxide (1 L) was added, the phases were stirred, allowed to settle, and then separated. Water (1 L) was added, the phases were stirred, allowed to settle, and then separated. The three aqueous extracts were tested by HPLC and no 16 was found, but the solution did contain unwanted impurities. The organic solution was then evaporated to give dry 16 base. The results are presented in Table 2.

TABLE 2

Synthesis of Compound 16.

| Expt # | Weight Yield | Percent Yield | W/W Assay (16) | W/W Assay (14) |
|---|---|---|---|---|
| 1 | 34.1 g | 88.1% | 72.7% | 5.4% |
| 2 | 33.9 g | 87.6% | * | * |
| 3** | 21.0 g | 68.0% | 81.0% | 5.0% |

\* Assay not run
\*\*Starting material was 40 g of compound 14

The three samples of 16 were combined. Anhydrous ethanol (1.25 L), water (0.25 L), and 48% HBr (55 mL) were added to the samples. The mixture was heated to boiling (78-80°) and stirred for one hour. All the solids dissolved and 400 mL of solvent was distilled. The solution was cooled to allow crystallization to begin. The slurry was cooled to 0-10° C. and stirred for two hours. The solids were separated by filtration, washed with anhydrous ethanol (100 mL) and then dried at 60° C. under partial vacuum. The yield of 16 HBr salt was 62.7 g. HPLC analysis indicated the purity was better than the existing standard. The filtrates (i.e., mother liquor and wash liquor) contained ~12 g of compound 16.

To prepare the HBr salt of 16, four additional samples of 16 (containing 84.8 g) were combined in a 2 L flask. Anhydrous ethanol (1.25 L), water (100 mL), and 48% HBr (55 mL) were added. The mixture was heated to reflux and ~400 mL of solvent was removed by distillation. The mixture was cooled to 0-5° C. and stirred for one hour. The slurry was filtered, the cake was washed with anhydrous ethanol (100 mL) and the solids dried at 60° C. in a vacuum oven. A yield of 62.7 g of 16.HBr was obtained at a HPLC purity of 99.4% area. A second crop of 7.5 g of 16.HBr was obtained from work-up of the filtrates. HPLC profile of 99.3% area was obtained.

Example 2a

Additional Syntheses of Compound 16

Additional reactions were performed in which compound 14 was contacted with HBr in the presence of mixtures of acetic acid and chloroform. These experiments revealed that the temperature of the reaction could be increased to between 0° C. and 5° C. upon addition of acetic acid to the organic solvent. Furthermore, the through-put of compound 16 increased. For example, the through-put was increased by about 4- to 5-fold when a 50:50 mixture of acetic acid and chloroform was used (see Table 3). Although 100% acetic acid had the best through-put, the isolated product had a low yield (60%).

TABLE 3

Solvent Composition, Reaction Temperature, and Yield.

| Wt compound 14 (g) | Add Temperature | Solvent | Wt to vol solvent | % recovery | Area % compound 16 | Note |
|---|---|---|---|---|---|---|
| 1.50 g | 0-5° C. | 100% $CHCl_3$ | 1 to 50 | 82% | 84.5% | 1 |
| 1.33 g | 0-5° C. | 5% HOAc/$CHCl_3$ | 1 to 30 | 83% | 77.4% | 1 |
| 1.92 g | 0-5° C. | 10% HOAc/$CHCl_3$ | 1 to 25 | 85% | 83.9% | 2 |
| 1.05 g | 0-5° C. | 25% HOAc/$CHCl_3$ | 1 to 20 | 84% | 80.0% | 2 |
| 2.09 g | 0-5° C. | 50% HOAc/$CHCl_3$ | 1 to 10 | 88% | 82.9% | 2 |
| 2.23 g | room temp | 100% HOAc | 1 to 7.5 | 90% | 82.8% | 2 |

Note:
1 = Aqueous NaOH added dropwise into reaction mixture.
2 = Reaction mixture added dropwise into aqueous NaOH.

Compound 14.HBr (2.09 g; 4.7 mmol), 50% glacial acetic acid in chloroform (21 mL) and 2 drops of 48% HBr were added to a three-necked round bottom flask. The mixture was cooled to 0-5° C. and bromine (0.376 g; 2.3 mmol) was added dropwise. The reaction was stirred for 50 minutes at 0° C. Then, bromine (0.376 g; 2.3 mmol) was added dropwise, and the reaction was stirred for 15 minutes at 5° C. Sodium hydroxide (12.0 g, 0.30 moles) was added to 100 mL of distilled water in a separate flask, and the mixture was cooled to 5° C. The reaction mixture was added dropwise to the NaOH solution over a one hour period and the temperature was kept below 10° C. The reaction mixture was warmed to room temperature. The mixture was transferred to a separatory funnel, and extracted with chloroform (3×10 mL). The organic phases were combined, dried over anhydrous $MgSO_4$ (2 g), filtered, and evaporated. Purified compound 16 (HBr salt, 2.0 g; 81% yield, 99 w/w % assay) was obtained from crystallization from methanol (5 mL), distilled water (5 mL), and 1 drop of 48% HBr. The crystals were isolated by filtration and were dried at 60° C. for 48 hr.

Example 3

Synthesis of Compound 19 from Compound 16

A 125 mL three-neck flask was equipped with a thermometer, a dropping funnel for addition of bromine ($Br_2$). Another dropping funnel connected to the top of condenser was used to collect the distilled solvent. The compound 16.HBr (5.50 g) was suspended in MeOH/CH(OMe)$_3$ (20 mL/20 mL) at room temperature. Sulfuric acid ($H_2SO_4$, 1.0 mL) was added (pH=0~0.5). The suspension was heated to reflux for 2 minutes, forming a solution at 55° C. Solvent (~20 mL) was removed by distillation at 88° C. in an oil bath for 15 minutes. Dichloroethane (bp: 83° C., 20 mL) was added. The mixture was heated over the 88° C. oil bath to distill off ~10 mL solvent over 10 minutes. $H_2SO_4$ (0.25 mL) was added (pH=0~1). A solution of $Br_2$ in $CHCl_3$ (0.70 mmol/mL, 19.6 mL, 1.1 eq, was diluted to 40 mL with $CHCl_3$) was added dropwise over 25 minutes. $H_2SO_4$ (0.25 mL) was added. 50 g of solution was obtained, of which 5 g was taken for another experiment and the rest of the reaction mixture (45 g) was cooled to room temperature for the following isolation of 19 acid salt.

The reaction mixture was evaporated on a Buchi rotary evaporator at 40° C. under maximum vacuum. Chloroform (ethanol free; 50 mL) and water (50 mL) were added to the residue. This mixture was stirred, allowed to settle, and the phases were separated. The aqueous phase was extracted twice more with chloroform (ethanol free; 5 mL). All of the chloroform extracts were combined and evaporated on the Buchi. Acetone (80 mL) was added to the evaporation residue and the stirred mixture was warmed to 45° C. A white precipitate formed after ~45 sec of stirring. The mixture was cooled to 0-5° C. and stirred for 30 min. The precipitate was filtered and the solids were washed with acetone (~5 mL). The solids were air dried, and 3.9 g of 19.$H_2SO_4$ at a HPLC profile of 95.3% area was recovered.

Example 4

Synthesis of Compound 20 from Compound 19

The compound, 19.$H_2SO_4$ (4.9 g), was suspended in tetrahydrofuran (THF) (50 mL). After flushing with nitrogen, tert-butoxide (t-BuOK) (7.0 g) was added. The mixture was stirred, heated at 65° C. for 1.5 h, and then cooled to room temperature. Water (200 mL) was added under nitrogen with stirring for 3 h. After the time period, the precipitate was separated by filtration and washed with water (2×30 mL). The wet solid was dried in flowing air for 2 h. The solid was suspended in acetonitrile (ACN) and reduced to dryness at 60° C. in vacuum for 2 h to give 2.85 g of compound 20 as a yellow solid (82% yield).

Example 5

Synthesis of Compound 21 from Compound 20

Compound 20 (2.85 g) was suspended in $Me_3SiCl$/ACN (8.5 m/20 mL) for 1 h. This suspension was added (1 mL each time) to a solution of $Me_3SiCl$ (8.5 mL) in ACN (40 mL) to form a new solution. Each aliquot of the suspension dissolved in 2~5 min after addition to the solution. The solution was stirred for another 30 min and after the complete addition of the suspension. The solution was then added to 10% $NH_4OH$ (240 mL) and extracted with $CHCl_3$ (2×50 mL). The organic layers were washed with water (2×100 mL), pumped down to dryness to give the product, 21, as 2.93 g of solid.

Example 6

Synthesis of Compound 23 from Compound 21

Compound 21 (~2.90 g) was dissolved in 29 mL HOAc/$H_2O$ (1:1) to form a solution. The solution was cooled to 5~10° C. and 32% peracetic acid ($CH_3CO_3H$) (in diluted HOAc) was added in three portions. The reaction mixture was stirred at room temperature for 30 min. Pd—C (5% Pd on carbon, 0.3 g) was added and stirred for 20 min to give a reaction mixture. HPLC analysis of the mixture revealed that compound 22 was the major product (>90% area/area). Additional Pd—C (5% Pd on carbon, 0.3 g) was added to the reaction mixture, which was heated at 60° C. under hydrogen (60 PSI) and stirred for 2 h. The reaction mixture was cooled to room temperature and filtered though ~10 g of silical gel. The solid was washed with 1% HOAc in MeOH (50 mL). The filtrate was reduced under vacuum to give an oil, which was dissolved in $CHCl_3$ (30 mL). Water (60 mL) was added, the phases were separated, and the aqueous phase as extracted with $CHCl_3$ (30 mL). The combined organic layers were washed with water (2×30 mL) and evaporated to give 1.29 g of the product, 23, as a solid.

Example 7

Synthesis of Compound 24 from Compound 23

Compound 23 (1.29 g solid) was dissolved in $CHCl_3$ to make 13.0 mL of solution. Part of the above solution (9.7 mL, containing ~0.98 g 23) was added to a solution of $BBr_3$ (2.82 mL) in $CHCl_3$ (10 mL) at 0-5° C. to form a suspension. The suspension was stirred at room temperature for 3 h, and 1 mL of the mixture was taken for HPLC sample before work up. The reaction mixture was stirred for a total of 5 h and then added to water (40 mL). Nitrogen was bubbled through the $CHCl_3$ layer until most of the $CHCl_3$ was removed by evaporation. The remaining mixture was washed with ether (3×40 mL), and then 4 N NaOH (10 mL) was added to the aqueous layer after extraction. The solution formed was washed with ether (3×40 mL). To the aqueous layer, HOAc was added until pH=9 (finally adjusted by adding c-$NH_4OH$). The solution was reduced to dryness under vacuum to give a sticky solid. The solid was suspended in 5% NH$_4$OH solution (20 mL), stirred for 30 minutes, and filtered. The solid was re-suspended in MeOH/H$_2$O (9 ml/6 mL). HOAc (0.4 mL) was added to form a solution. A precipitate formed upon addition of c-NH$_4$OH to pH=9. The mixture was stirred at 5° C. for 1 h, and the solid was separated by filtration. After washing with water and drying in an air-flow overnight, 0.61 g of an off-white solid remained. The solid was dried in high vacuum at 60° C. for 3 h to give 0.56 g of the product, 24, as an off-white solid.

What is claimed is:

1. A compound comprising of Formula 21a:

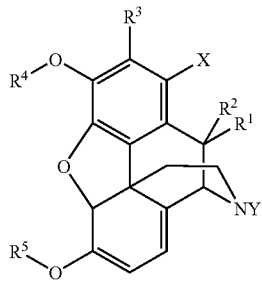

21a wherein:
R$^1$ and R$^2$ are independently chosen from hydrogen, OH, NH$_2$, SH, CF$_3$, hydrocarbyl, substituted hydrocarbyl, alkyl ketal, alkyl thiol ketal, and alkyl dithiol ketal, wherein when R$^1$ and R$^2$ are different they form an epimeric pair, and wherein R$^1$ and R$^2$ together may form a group chosen from =O, =S, cycloalkyl ketal, cycloalkyl thiol ketal, and cycloalkyl dithiol ketal;

R$^3$ is chosen from hydrogen, halogen, OH, NH$_2$, CN, CF$_3$, SO$_2$R$^8$, hydrocarbyl, and substituted hydrocarbyl;

R$^4$ and R$^5$ are independently chosen from —(CH$_2$)$_n$CH$_3$ and CH$_3$;

R$^8$ is chosen from hydrocarbyl and substituted hydrocarbyl;

X is halogen;

Y is chosen from a benzyloxycarbonyl group, an alkylamidocarbonyl group, a trialkylsilyl group, an alkylsulfonyl group, and an aryl sulfonyl group; and n is an integer from 1 to 8.

2. The compound of claim 1, wherein:
R$^1$, R$^2$, and R$^3$ are each hydrogen;
R$^4$ and R$^5$ are each CH$_3$;
X is bromine; and
Y is chosen from —Si(CH$_3$)$_3$, and —SO$_2$CH$_3$.

3. The compound of claim 1, wherein the optical activity of the compound is (+) or (−), and the configuration of C-5, C-13, and C-9, respectively, of the compound may be RRR, RRS, RSR, RSS, SRR, SRS, SSR, or SSS, provided that the C-15 and the C-16 carbons are both either on the alpha face or the beta face of the molecule.

4. A process for the preparation of compound 21a, the process comprising the following reaction scheme:

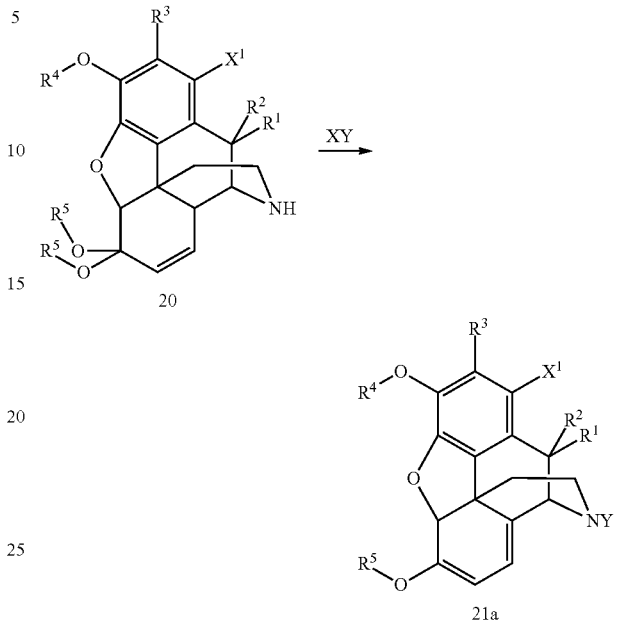

wherein:
R$^1$ and R$^2$ are independently chosen from hydrogen, OH, NH$_2$, SH, CF$_3$, hydrocarbyl, substituted hydrocarbyl, alkyl ketal, alkyl thiol ketal, and alkyl dithiol ketal, wherein when R$^1$ and R$^2$ are different they form an epimeric pair, and wherein R$^1$ and R$^2$ together may form a group chosen from =O, =S cycloalkyl ketal, cycloalkyl thiol ketal, and cycloalkyl dithiol ketal;

R$^3$ is chosen from hydrogen, halogen, OH, NH$_2$, CN, CF$_3$, SO$_2$R$^8$, hydrocarbyl, and substituted hydrocarbyl;

R$^4$ and R$^5$ are independently chosen from —(CH$_2$)$_n$CH$_3$, and CH$_3$;

R$^8$ is chosen from hydrocarbyl and substituted hydrocarbyl;

X and X$^1$ are independently halogen;

Y is chosen from a benzyloxycarbonyl group, an alkylamidocarbonyl group, a trialkylsilyl group, an alkylsulfonyl group, and an aryl sulfonyl group;

m is an integer from 1 to 3; and n is an integer from 1 to 8.

5. The process of claim 4, wherein:
YX is chosen from (CH$_3$)$_3$SiCl, POCl$_3$, and CH$_3$SO$_2$Cl;
R$^1$, R$^2$, and R$^3$ are each hydrogen;
R$^4$ and R$^5$ are each CH$_3$; and
X$^1$ is bromine.

6. The process of claim 4, wherein the molar/molar ratio of compound 20 to YX is from about 1:1 to about 1:50, the reaction is conducted in the presence of an aprotic solvent, and the reaction is conducted at a temperature ranging from about 0° C. to about 80° C.

7. The process of claim 4, wherein the yield of compound 21 is from about 60% to about 90%.

8. The compound of claim 1 wherein Y is a benzyloxycarbonyl group.

9. The compound of claim 1 wherein Y is an alkylamidocarbonyl group.

10. The compound of claim 1 wherein Y is a trialkylsilyl group.

11. The compound of claim 1 wherein Y is an alkylsulfonyl group.

12. The compound of claim 1 wherein Y is an aryl sulfonyl group.

13. The process of claim 4 wherein Y is a benzyloxycarbonyl group.

14. The process of claim 4 wherein Y is an alkylamidocarbonyl group.

15. The process of claim 4 wherein Y is a trialkylsilyl group.

16. The process of claim 4 wherein Y is an alkylsulfonyl group.

17. The process of claim 4 wherein Y is an aryl sulfonyl group.

* * * * *